United States Patent [19]
Aloup et al.

[11] Patent Number: 5,922,716
[45] Date of Patent: Jul. 13, 1999

[54] 5H-INDENO[1,2-B]PYRAZINE-2,3-DIONE DERIVATIVES, THEIR PREPARATION AND MEDICINAL PRODUCTS CONTAINING THEM

[75] Inventors: Jean-Claude Aloup, Villeneuve le Roi; François Audiau, Charenton le Pont; Michel Barreau, Montgeron; Dominique Damour, Orly; Arielle Genevois-Borella, Thiais; Patrick Jimonet, Villepreux; Serge Mignani, Chatenay-Malabry; Yves Ribeill, Villemoisson sur Orge, all of France

[73] Assignee: Rhone-Poulenc Rorer S.A., Antony, France

[21] Appl. No.: 08/714,164

[22] PCT Filed: Mar. 23, 1995

[86] PCT No.: PCT/FR95/00359

§ 371 Date: Sep. 27, 1996

§ 102(e) Date: Sep. 27, 1996

[87] PCT Pub. No.: WO95/26342

PCT Pub. Date: Oct. 5, 1995

[30] Foreign Application Priority Data

Mar. 28, 1994 [FR] France ................. 94 03583

[51] Int. Cl.$^6$ ............ C07D 487/04; C07D 241/38; C07D 247/02; A61K 31/495
[52] U.S. Cl. ............... 514/250; 544/344; 544/345; 548/484; 564/200; 564/428
[58] Field of Search ............... 544/344; 514/250

[56] References Cited

U.S. PATENT DOCUMENTS

| | | | |
|---|---|---|---|
| 4,354,027 | 10/1982 | Loev et al. | 544/346 |
| 4,400,382 | 8/1983 | Brown et al. | 544/353 |
| 4,507,300 | 3/1985 | Brown et al. | 514/280 |
| 4,668,678 | 5/1987 | Brown et al. | 514/250 |
| 5,153,196 | 10/1992 | McQuaid et al. | 514/250 |
| 5,196,421 | 3/1993 | McQuaid et al. | 514/250 |
| 5,468,748 | 11/1995 | Faarup | 544/344 |

FOREIGN PATENT DOCUMENTS

| | | |
|---|---|---|
| 2696466 | 4/1994 | France . |
| 2707645 | 1/1995 | France . |
| WO9306103 | 4/1993 | WIPO . |
| WO9400124 | 1/1994 | WIPO . |
| WO9418175 | 8/1994 | WIPO . |
| WO9502601 | 1/1995 | WIPO . |

OTHER PUBLICATIONS

Derwent Abstract of FR-A-2 696 466. (1994).

Derwent Abstract of FR-A-2 707 645. (1995).

McQuaid et al., "Synthesis and Excitatory Amino Acid Pharmacology of a Series of Heterocyclic-Fused Quinoxalinones and Quinazolinones", J. Med. Chem., 35(18):3319-3324 (1992).

Rashet et al., "A Facile Synthesis of Novel Triazoloquinoxalines and Triazinoquinozalinones [1]", J. Of Heterocyclic Chemistry, 27(3):691-694 (1990).

*Primary Examiner*—Mark L. Berch
*Attorney, Agent, or Firm*—Finnegan, Henderson, Farabow, Garrett & Dunner, L.L.P.

[57] ABSTRACT

Compounds of formula (I):

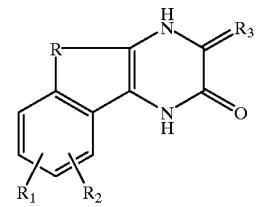

wherein R represents a $CR_4R_5$, $CHR_6$, or $C=R_7$ radical and $R_3$ represents an oxygen atom, salts thereof, the preparation thereof and drugs containing same. The compounds of formula (I) have valuable pharmacological properties and are alpha-amino-3-hydroxy-5-methyl-4-osoxaziepropionic acid (AMPA) receptor antagonists, said receptor also being known as the quisqualate receptor. Furthermore, the compounds of formula (I) are non-competitive N-methyl-D-aspartate (NMDA) receptor antagonists, and particularly NMDA receptor glycine modulation site ligands.

6 Claims, No Drawings

5H-INDENO[1,2-B]PYRAZINE-2,3-DIONE DERIVATIVES, THEIR PREPARATION AND MEDICINAL PRODUCTS CONTAINING THEM

The present invention relates to compounds of formula:

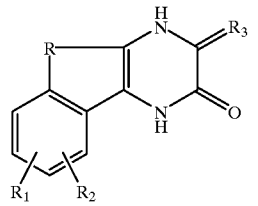

(I)

and their salts, to their preparation and to medicinal products containing them.

In the formula (I),

— R represents an N-alk, C(R$_4$)R$_5$, CH—R$_6$ or C=R$_7$ radical,

— R$_1$ and R$_2$, which may be identical or different, represent hydrogen or halogen atoms or alkyl, alkoxy, amino, —N=CH—N(alk)alk', nitro, cyano, phenyl, imidazolyl, SO$_3$H, hydroxyl, polyfluoroalkoxy, carboxyl, alkoxycarbonyl, —NH—CO—NR$_{11}$R$_{12}$, —N(alk)—CO—NR$_{11}$R$_{12}$, —N(alk-Ar)—CO—NR$_{11}$R$_{12}$, —NH—CS—NR$_{11}$R$_{12}$, —N(alk)-CS—NR$_{11}$R$_{12}$, —NH—CO—R$_{11}$, —NH—CS—R$_{24}$, —NH—C(=NR$_{27}$)—NR$_{10}$R$_{12}$, —N(alk)—C(=NR$_{27}$)—NR$_{10}$R$_{12}$, —CO—NR$_{10}$R$_{12}$, —NH—SO$_2$—NR$_{10}$R$_{12}$, —N(alk)—SO$_2$—NR$_{10}$R$_{12}$, —NH—SO$_2$—CF$_3$, —NH—SO$_2$-alk, —NR$_{10}$R$_{13}$, —S(O)$_m$-alk-Ar or —SO$_2$—NR$_{10}$R$_{12}$ radicals or 2-oxo-1-imidazolidinyl radicals in which position 3 is optionally substituted with an alkyl radical or 2-oxo-1-perhydropyrimidinyl radicals in which position 3 is optionally substituted with an alkyl radical, — R$_3$ represents an oxygen atom or an NOH, NOalk or NOalkAr radical, — R$_4$ represents an alkyl, -alk-Het or phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, — R$_5$ represents an alkyl (1–11C in an unbranched or branched chain), -alk-Het, —NR$_8$R$_9$, —NH—CHO, —NH—COOR$_{17}$, —NH—SO$_2$R$_{24}$, —COOR$_{10}$, -alk-COOR$_{10}$, -alk-CONR$_{10}$R$_{18}$, -alk-NR$_{10}$R$_{18}$, -alk-OH or -alk-CN radical, a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, an —NH—CO—Ar radical in which Ar is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, an —NH—CO-Het, —NH—CO-alk-Het, —NH—CO-alk-COOR$_{10}$ or —NH—CO-alk-NR$_{10}$R$_{18}$ radical, an —NH—CO-alk-Ar radical in which Ar is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, a 1-pyrrolyl radical optionally substituted with a —COOR$_{10}$ radical, an —NH—CO—NH-alk-Ar radical in which Ar is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, an —NH—CO—NH-Het or —NH—CO—NH-alk-Het radical, an —NH—CO—NH—Ar radical in which Ar is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, or an —NH—COalk, —NH—Cocycloalkyl, —NH—CO—NH-alk or —NH—CO—NH$_2$ radical, or alternatively R$_4$ and R$_5$, together with the carbon atom to which they are attached, form a cycloalkyl radical, — R$_6$ represents a hydrogen atom or a hydroxyl, alkyl (1–11C in an unbranched or branched chain), -alk-OH, —NR$_{14}$R$_{15}$, -alk-NR$_{14}$R$_{15}$, -alk-Het, —NH—CHO, —COOalk, -alk-COOR$_{10}$ or -alk-CO—NR$_{10}$R$_{18}$ radical, a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, an —R$_{16}$—COOR$_{10}$ or —CO—COOR$_{10}$ radical or a 1-pyrrolyl radical optionally substituted with a —COOR$_{10}$ radical, — R$_7$ represents an oxygen atom or an NOH, NO-alk-COOR$_{10}$, NO-alk, CHR$_{19}$, NR$_{10}$, C(COOR$_{10}$)R$_{20}$ or C(CONR$_{10}$R$_{21}$)R$_{20}$ radical, — R$_8$ represents a hydrogen atom or an alkyl, -alk-COOR$_{10}$, -alk-NR$_{10}$R$_{21}$ or -alk-Het radical or a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, — R$_9$ represents a hydrogen atom or an alkyl radical, — R$_{10}$ represents a hydrogen atom or an alkyl radical, — R$_{11}$ represents a hydrogen atom or an alkyl (1–9C in an unbranched or branched chain), alkoxy, -alk-COOR$_{10}$, -alk-Het or -alk-NR$_{12}$R$_{10}$ radical, a phenylalkyl radical in which the phenyl ring is optionally substituted with one or more substituents chosen from halogen atoms and alkyl, alkoxy, nitro, amino, hydroxyl, -alk-NH$_2$, carboxyl, alkoxycarbonyl, cyano and -alk-COOR$_{10}$ radicals, a phenyl radical optionally substituted with one or more substituents chosen from halogen atoms and alkyl, alkoxy, nitro, amino, hydroxyl, -alk-NH$_2$, carboxyl, alkoxycarbonyl, cyano and -alk-COOR$_{10}$ radicals, or a -Het radical, — R$_{12}$ represents a hydrogen atom or an alkyl radical, — R$_{13}$ represents an alkyl, Het or alkoxycarbonyl radical, — R$_{14}$ and R$_{15}$, which may be identical or different, each represent an alkyl radical, or alternatively R$_{14}$ represents a hydrogen atom and R$_{15}$ represents a hydrogen atom or an alkyl, —COR$_{22}$, —CSR$_{23}$ or —SO$_2$R$_{24}$ radical, — R$_{16}$ represents a —CHOH or —CH(OH)alk(1–5C)-chain, — R$_{17}$ represents an alkyl or phenylalkyl radical, — R$_{18}$ represents a hydrogen atom or an alkyl radical, — R$_{19}$ represents a hydroxyl, alkyl, -alk-Het, —NR$_{25}$R$_{26}$, -alk-COOR$_{10}$ or -Het radical, a phenyl radical optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, or a phenylalkyl radical in which the phenyl ring is optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, —R$_{20}$ represents a hydrogen atom or an alkyl radical, —R$_{21}$ represents a hydrogen atom or an alkyl radical, —R$_{22}$ represents an alkyl, cycloalkyl, —COOalk or -alk-COOR$_{10}$ radical, a phenyl radical optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, a phenylalkyl radical in which the phenyl ring is optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, an -alk-NR$_{10}$R$_{12}$ radical, an —NH—Ar radical in which Ar is optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, a -Het, -alk-Het or —OR$_{17}$ radical, an —NH-alk-Ar radical in which Ar is optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, or an —NH-alk-Het, —NH-alk, —NH$_2$ or —NH-Het radical, —R$_{23}$ represents an —NH-alk, —NH—Ar, —NH-Het or —NH$_2$ radical, —R$_{24}$ represents an alkyl or phenyl radical, —R$_{25}$ and R$_{26}$, which may be identical or different, each represent an alkyl or cycloalkyl radical, —R$_{27}$ represents a hydrogen atom or an alkyl radical, -alk represents an alkyl or alkylene radical, -alk' represents an alkyl radical, —m is equal to 0, 1 or 2, —Ar represents a phenyl radical, -Het represents a saturated or unsaturated, mono- or polycyclic heterocycle containing 1 to 9 carbon atoms and one or more hetero atoms (O, S, N), optionally substituted with one or more alkyl, phenyl or phenylalkyl radicals, on the understanding that, when R$_1$ and R$_2$ represent hydrogen atoms and R$_3$ represents an oxygen atom, R is not a radical (a) C═R$_7$ in which R$_7$ represents an oxygen atom or an NOH radical, or (b) CH—R$_6$ for which R$_6$ represents a hydroxyl radical.

Except where otherwise stated, in the foregoing definitions and those which follow, the alkyl, alkylene and alkoxy radicals and portions contain 1 to 6 carbon atoms and are unbranched- or branched-chain radicals, the acyl radicals and portions contain 2 to 4 carbon atoms, the cycloalkyl radicals contain 3 to 6 carbon atoms and halogen atoms are chosen from fluorine, chlorine, bromine and iodine.

Preferably, Het is chosen from pyrrolyl, pyridyl, pyrimidinyl, imidazolyl, thiazolyl, oxazolinyl, thiazolinyl, pyrazinyl, tetrazolyl, triazolyl, pyrrolidinyl, piperazinyl, piperidyl, thienyl, furyl, azetidinyl and imidazolinyl rings, all these heterocycle being optionally substituted with one or more alkyl, phenyl or phenylalkyl radicals. Preferred substituents are methyl, phenyl and benzyl radicals.

Preferred polyfluoroalkoxy radicals are trifluoromethoxy radicals.

The compounds of formula (I) for which R represents a C═R$_7$ radical for which R$_7$ represents an NO-alk, C(COOR$_{10}$)R$_{20}$ or C(CONR$_{10}$R$_{21}$)R$_{20}$ or CHR$_{19}$ radical and/or R$_3$ represents an NOH, NOalk or NOalkAr radical possess isomeric forms (E and Z). These isomers and the mixtures thereof form part of the invention.

The compounds of formula (I) for which R represents a CH—R$_6$ radical and R$_6$ represents a —CO—COOR$_{10}$ radical possess tautomeric forms (E and Z). These tautomeric forms also form part of the invention.

The enantiomers and diastereoisomers of the compounds of formula (I) for which R represents a C(R$_4$)R$_5$ or CH—R$_6$ radical also form part of the invention.

The compounds of formula (I) for which R represents an N-alk, C(R$_4$)R$_5$ or CH—R$_6$ radical, R$_6$ represents a hydrogen atom and R$_3$ represents an oxygen atom may be prepared by cyclization, in the presence of ammonium acetate, of a derivative of formula:

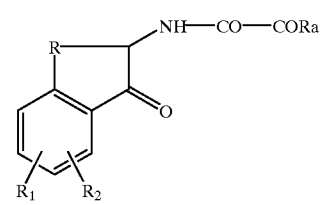

(II)

in which R represents an N-alk or C(R4)R$_5$ radical or a CH—R$_6$ radical in which R$_6$ represents a hydrogen atom, R$_1$ and R$_2$ have the same meanings as in the formula (I) and Ra represents an alkoxy radical.

This reaction is preferably performed in acetic acid, at the boiling point of the reaction medium.

The derivatives of formula (II) may be obtained by the action of a chloride ClCOCORa in which Ra is an alkoxy radical on a derivative of formula:

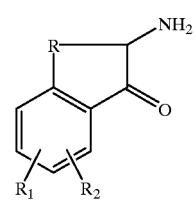

(III)

in which R represents an N-alk or C(R$_4$)R$_5$ radical or a CH—R$_6$ radical in which R$_6$ represents a hydrogen atom and R$_1$ and R$_2$ have the same meanings as in the formula (I).

This reaction is generally performed in an inert solvent such as tetrahydrofuran, in the present of a tertiary amine such as triethylamine, at a temperature of between 0 and 25° C.

The derivatives of formula (III) may be obtained by application or adaptation of the methods described in the examples and by P. W. NEBER et al., Justus Liebigs Ann. Chem., 526, 277 (1936), V. S. VELEZHEVA et al., Khim. Farm. Zh., 24, 46 (1990) (Chem. Abstracts, 114, 228786) and YUHPYNG L. CHEN et al., J. Med. Chem., 35(8), 1429 (1992).

The compounds of formula (I) for which R represents an N-alk radical or a CH—R$_6$ radical in which R$_6$ represents a hydrogen atom and R$_3$ represents an NOH, NOalk or NOalkAr radical may be prepared by the action of a corresponding compound of formula (I) for which $R_3$ represents an oxygen atom on a derivative $H_2NORb$ in which Rb represents a hydrogen atom or an alkyl radical or an -alkAr radical in which radicals alk and Ar have the same meanings as in the formula (I).

This reaction is generally performed in an inert solvent such as an alcohol (for example ethanol), dioxane or water, at the boiling point of the reaction medium.

The compounds of formula (I) for which R represents a $C=R_7$ radical in which $R_7$ represents an oxygen atom may be prepared by hydrolysis of the corresponding compounds of formula (I) for which R represents a $C=R_7$ radical and $R_7$ represents an NOH radical.

This reaction is generally performed by means of an acid, in an aqueous medium, at the boiling point of the reaction medium. As an acid, hydrochloric acid is preferably used.

The compounds of formula (I) for which R represents a $C=R_7$ radical and $R_7$ represents an NOH radical may be prepared by the action of an alkyl nitrite on a corresponding compound of formula (I) for which R represents a $CH-R_6$ radical and $R_6$ represents a hydrogen atom.

This reaction is preferably performed in an inert solvent such as dimethyl sulphoxide, in the presence of an alkali metal hydride such as sodium hydride, at a temperature in the region of 20° C. Preferably, isoamyl nitrite is used.

The compounds of formula (I) for which R represents a $C=R_7$ radical and $R_7$ represents an NO-alk-$COOR_{10}$ or NO-alk radical may be prepared by the action of a corresponding compound of formula (I) for which R represents a $C=R_7$ radical and $R_7$ represents an NOH radical on a halide Hal-Rc for which Hal represents a halogen atom and Rc represents an alkyl or -alk-$COOR_{10}$ radical, alk and $R_{10}$ having the same meanings as in the formula (I).

This reaction is preferably performed in the presence of a base such as an alkali metal hydride, for instance sodium hydride, in an inert solvent such as dimethyl sulphoxide, at a temperature in the region of 20° C.

The derivatives Hal-Rc for which Rc represents an -alk-$COOR_{10}$ radical are commercially available or may be obtained by the action of Hal-alk-Hal in which Hal represents a halogen atom and alk represents an alkyl radical on an alkali metal cyanide (sodium or potassium cyanide), in a water/alcohol mixture, at a temperature between 0° C. and the boiling point of the reaction medium, followed by the action of a strong acid such as hydrochloric acid, in the presence of an alcohol (for example methanol, ethanol), at a temperature between 0° C. and the boiling point of the reaction medium.

The compounds of formula (I) for which R represents a $C=R_7$ radical and $R_7$ represents a $CHR_{19}$ radical in which $R_{19}$ represents a hydroxyl radical may be prepared by hydrolysis of the corresponding compounds of formula (I) for which $R_{19}$ represents an $-NR_{25}R_{26}$ radical.

This reaction is preferably performed by means of an acid such as hydrochloric acid, in an aqueous medium, at a temperature of between 20 and 40° C.

The compounds of formula (I) for which R represents a $C=R_7$ radical and $R_7$ represents a $CHR_{19}$ radical in which $R_{19}$ represents an $-NR_{25}R_{26}$ radical may be prepared by the action of a corresponding compound of formula (I) for which R represents a $-CH-R_6$ radical and $R_6$ represents a hydrogen atom on a derivative HC (Rd) (Re) Rf in which either Rd and Rf, which may be identical or different, each represent an $-NR_{25}R_{26}$ radical in which $R_{25}$ and $R_{26}$ have the same meanings as in the formula (I) and Re represents an alkoxy radical such as a tert-butoxy radical, or Rd, Re and Rf, which are identical, each represent an $-NR_{25}R_{26}$ radical in which $R_{25}$ and $R_{26}$ have the same meanings as in the formula (I).

This reaction is generally performed in an inert solvent such as dimethylformamide, at a temperature of between 20 and 40° C.

The derivatives HC (Rd) (Re) Rf may be obtained by application of adaptation or the method described by H. BREDERECK, Liebigs Ann. Chem., 762, 62 (1972).

The compounds of formula (I) for which R represents a $C=R_7$ radical, $R_7$ represents a $CHR_{19}$ radical and $R_{19}$ represents an alkyl, optionally substituted phenyl or -alk-Het radical, a phenylalkyl radical in which the phenyl ring is optionally substituted or a -Het or -alk-$COOR_{10}$ radical may be prepared by the action of a corresponding compound of formula (I) for which R represents a $CH-R_6$ radical and $R_6$ represents a hydrogen atom on an aldehyde of formula OHC—Rg in which Rg represents an alkyl radical, a phenyl radical optionally substituted with one or more substituents chosen from halogen atoms and alkyl, alkoxy, nitro, amino, hydroxyl, -alk-$NH_2$, —$COOR_{10}$, cyano and -alk-$COOR_{10}$ radicals, an -alk-Het radical, a phenylalkyl radical in which the phenyl ring is optionally substituted with one or more substituents chosen from halogen atoms and alkyl, alkoxy, nitro, amino, hydroxyl, -alk-$NH_2$, —$COOR_{10}$, cyano and -alk-$COOR_{10}$ radicals, or a -Het or -alk-$COOR_{10}$ radical in which radicals alk, Het and $R_{10}$ have the same meanings as in the formula (I).

This reaction is generally performed either in an inert solvent such as dimethylformamide, 1,2-dimethoxyethane, a lower aliphatic alcohol (for example methanol, ethanol) or a mixture of these solvents, in the presence of a base such as sodium hydroxide, potassium hydroxide or a strong organic base such as 1,8-diazabicyclo[5.4.0]undec-7-ene, at a temperature of between 20 and 100° C., or in dimethyl sulphoxide, in the presence of an alkali metal hydride such as sodium hydride, at a temperature in the region of 20° C., or in the presence of tetrabutylammonium bromide and a base such as an alkali metal hydroxide (for example sodium hydroxide, potassium hydroxide), in dimethyl sulphoxide, at a temperature between 20° C. and the boiling point of the reaction medium, or in acetic acid or acetic anhydride, in the presence of ammonium acetate, at a temperature between 20° C. and the boiling point of the reaction medium.

The derivatives OHC—Rg are commercially available or may be obtained (a) by oxidation of the corresponding alcohols $HOH_2C$—Rg (using $K_2Cr_2O_7$ in a sulphuric acid medium; $CrO_3$ in pyridine or $MnO_2$ in a chlorinated solvent (for example dichloromethane) at a temperature in the region of 20° C., or using dimethyl sulphoxide and ClCO—COCl by adaptation or application of the method described by D. SWERN et al., J. Org. Chem., 44, 4148 (1979)); (b) by reduction of the corresponding carboxylic acids HOOC—Rg (using lithium aluminum hydride or $AlH_3$, in an inert solvent such as tetrahydrofuran, at a temperature of between 0 and 25° C.); (c) by reduction of the corresponding esters alkOOC—Rg (using diisobutylaluminium hydride, in an inert solvent such as toluene, at a temperature of between −70° C. and 25° C., or lithium aluminum hydride, in an inert solvent such as tetrahydrofuran, at a temperature of between 0 and 25° C.).

The corresponding alcohols $HOH_2C$—Rg for which Rg represents an -alk-Het radical or an alk—Ar radical in which Ar is optionally substituted are commercially available or may be obtained from the corresponding organometallic compounds by application or adaptation of the methods described by N. S. NARASIMHAN et al., Tetrahedron Lett., 22 (29), 2797 (1981); L. ESTEL et al., J. Het. Chem., 26, 105 (1989); N. S. NARASIMHAN et al., Synthesis, 957 (1983); H. W. GSCHWEND et al., Organic reactions, 26, I (1979);

V. SNIEKUS, Chem. Rev., 90, 879 (1990) and F. MARSAIS et al., J. Heterocyclic Chem., 25, 81 (1988). Preferably, the organolithium or organomagnesium derivative of the heterocycle or of the optionally substituted benzene is reacted with formaldehyde, ethylene oxide or a derivative Hal-alk-CH$_2$OP where P is a protective group (for example methyl ether, tetrahydropyranyl ether, benzyl ether or triethylsilyl ether), Hal is a halogen atom and alk an alkyl radical, followed by liberation of the alcohol function, by application or adaptation of the methods described by W. GREENE et al., Protecting Groups in Organic Synthesis, second edition, 1991, John Wiley ans sons.

The corresponding alcohols HOH$_2$C—Rg for which Rg represents an -alk-Het radical or an -alk-Ar radical in which Ar is optionally substituted may also be obtained by reduction of the corresponding carboxylic acids or esters by means of lithium aluminum hydride, in an inert solvent such as tetrahydrofuran or diethyl ether, at the boiling point of the reaction medium.

The alcohols HOH$_2$C—Rg for which Rg represents an -alk-Het radical may also be obtained by application or adaptation of the method described by J. Th. MEYER et al., Helv. Chim. Acta, 65, 1868 (1982), from the derivatives Hal-H$_2$C-alk(0–5C)-Het, which are themselves obtained by the action of a halogenating agent, (halogenated derivative of phosphorus or thionyl chloride) from a corresponding derivative HOH$_2$C-alk(0–5C)-Het, optionally in an inert solvent such as dichloromethane, at a temperature of between 20 and 40° C.

The corresponding carboxylic acids HOOC—Rg for which Rg represents a -Het or -alk-Het radical or an -alk-Ar radical in which Ar is optionally substituted are commercially available or may be obtained from the corresponding optionally substituted benzenes and heterocycles by application or adaptation of the methods described by L. ESTEL et al., J. Heterocyclic Chem., 26, 105 (1989); N. S. NARASIM HAN et al., Synthesis, 957 (1983); A. TURCK et al., Synthesis, 881 (1988); A. J. CLARKE et al., Tetrahedron Lett, 27, 2373 (1974); A. R. KATRITZKY et al., Org. Perp. Procedure Int., 20 (6), 585 (1988); N. FURUKAWA et al., Tetrahedron Lett., 28 (47), 5845 (1987); H. W. GSCHWEND et al., Organic Reactions, 26, 1 (1979) and V. SNIECKUS, Chem. Rev., 90, 879 (1990). Preferably, the corresponding organometallic derivative of the heterocycle or of the corresponding optionally substituted benzene (for example organolithium, organomagnesium derivative) is prepared and reacted either with CO$_2$ or with a derivative Hal-alk-COOalk in which Hal represents a halogen atom and alk an alkyl radical, followed by a hydrolysis of the ester.

The derivatives Hal-alk-COOalk are commercially available or prepared by the action of Hal-alk-Hal in which Hal represents a halogen atom on an alkali metal cyanide such as sodium or potassium cyanide, in a water/alcohol mixture, at a temperature between 0° C. and the boiling point of the reaction medium, followed by the action of an acid such as hydrochloric acid, in the presence of an alcohol, at a temperature between 0° C. and the boiling point of the reaction medium.

The corresponding esters alkOOC—Rg are commercially available or may be obtained from the acids by the action of an organic acid such as hydrochloric acid or sulphuric acid, in the alcohol also serving as esterifying agent, at the boiling point of the reaction medium.

The derivatives Hal-alk-Hal are commercially available or may be obtained from the corresponding dihydric alcohols by application or adaptation of the methods described by C. LAROCK, "Comprehensive Organic Transformations", Ed. VHC, page 353 (1989).

The derivatives HOC—Rg for which Rg represents an -alk-COOR$_{10}$ radical are commercially available or may be obtained by reduction of the corresponding carboxylic acids, by application or adaptation of the methods described by H. C. BROWN et al., J. Am. Chem. Soc., 106, 8001 (1984) and J. Org. Chem., 52, 5400 (1987). The corresponding acids are commercially available or may be obtained by application or adaptation of the methods described by H. HUNSDIECKER et al., Chem. Ber., 75, 256 (1942) and R. F. NAYLOR, J. Chem. Soc., 1108 (1947).

The compounds of formula (I) in which R represents a C=R$_7$ radical and R$_7$ represents an NRIo radical may be prepared by the action of ethyl trifluoroacetate on a corresponding compound of formula (I) for which R represents a CH—R$_6$ radical, R$_6$ represents an —NR$_{14}$R$_{15}$ radical, R$_{14}$ represents a hydrogen atom and R$_{15}$ represents a hydrogen atom or an alkyl radical.

This reaction is generally performed in an inert solvent such as dimethylformamide, at a temperature in the region of 60° C.

The compounds of formula (I) for which R represents a C=R$_7$ radical and R$_7$ represents a C(COOR$_{10}$)R$_{20}$ radical may be prepared by dehydration of a derivative of formula:

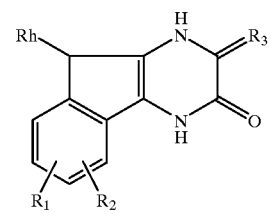

(IV)

in which R$_1$, R$_2$ and R$_3$ have the same meanings as in the formula (I) and Rh represents a —C(R$_{20}$) (OH)—COOR$_{10}$ radical in which R$_{20}$ and R$_{10}$ have the same meanings as in the formula (I).

This reaction is generally performed in acetic anhydride, at the boiling point of the reaction medium.

The derivatives of formula (IV) for which R$_1$, R$_2$ and R$_3$ have the same meanings as in the formula (I) and Rh represents a —C(R$_{20}$) (OH)—COOR$_{10}$ radical in which R$_{20}$ and R$_{10}$ have the same meanings as in the formula (I) may be obtained by the action of a corresponding compound of formula (I) for which R represents a CH—R$_6$ radical and R$_6$ represents a hydrogen atom on a derivative R$_{20}$—CO—COOR$_{10}$ for which R$_{10}$ and R$_{20}$ have the same meanings as in the formula (I), followed by treatment with acetic acid.

This reaction is performed in dimethyl sulphoxide, in the presence of an alkali metal hydride such as sodium hydride, at a temperature in the region of 20° C., or in the presence of tetrabutylammonium bromide and a base such as an alkali metal hydroxide (for example sodium hydroxide, potassium hydroxide), in dimethyl sulphoxide, at a temperature of between 20 and 100° C. The acetic acid treatment is performed at a temperature below 20° C.

The derivatives of formula R$_{20}$—CO—COOR$_{10}$ in which R$_{10}$ and R$_{20}$ have the same meanings as in the formula (I) are commercially available or may be obtained by application or adaptation of the methods described by L. A. CARPINO, J. Org. Chem., 29, 2820 (1964) and H. H. WASSERMAN, J. Org. Chem., 50, 3573 (1985).

The compounds of formula (I) for which R represents a C=R$_7$ radical and R$_7$ represents a C(CONR$_{10}$R$_{21}$)R$_{20}$ radical may be prepared by the action of a corresponding compound of formula (I) for which R represents a C=$R_7$ radical and $R_7$ represents a C(COOR$_{10}$)$R_{20}$ radical on an amine HNR$_{10}$R$_{21}$ in which $R_{10}$ and $R_{21}$ have the same meanings as in the formula (I).

When the acid is employed, the reaction is performed in the presence of a condensing agent used in peptide chemistry, such as a carbodiimide (for example N,N'-dicyclohexylcarbodiimide) or N,N'-carbonyldiimidazole, in an inert solvent such as an ether (for example tetrahydrofuran, dioxane), an amide (dimethylformamide) or a chlorinated solvent (for example methylene chloride, 1,2-dichloroethane, chloroform), at a temperature between 0° C. and the refluxing temperature of the reaction mixture. When an ester is employed, the reaction is then performed either in an organic medium, optionally in the presence of an acceptor for acid such as a nitrogenous organic base (for example trialkylamine, pyridine, 1,8-diazabicyclo[5.4.0]undec-7-ene or 1,5-diazabicyclo[4.3.0]non-5-ene), in a solvent such as is mentioned above, or a mixture of these solvents, at a temperature between 0° C. and the refluxing temperature of the reaction mixture, or in a two-phase aqueous-organic medium in the presence of an alkali metal base or alkaline-earth metal base (sodium hydroxide, potassium hydroxide) or an alkali metal carbonate or bicarbonate or alkaline-earth metal carbonate or bicarbonate, at a temperature of between 0 and 40° C.

The compounds of formula (I) for which R represents a C($R_4$)$R_5$ radical, $R_4$ represents an alkyl or -alk-Het radical or a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals and $R_5$ is identical to $R_4$ may be prepared by the action of a corresponding compound of formula (I) for which R represents a CH—$R_6$ radical and $R_6$ represents a hydrogen atom on a halide of formula Hal-Ri in which Ri represents an alkyl or -alk-Het radical or a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, alk, Het and $R_{10}$ having the same meanings as in the formula (I).

This reaction is preferably performed in an inert solvent such as dimethyl sulphoxide, dimethylformamide, tetrahydrofuran or dioxane, in the presence of a base such as an alkali metal hydroxide (for example sodium hydroxide, potassium hydroxide), optionally in the presence of tetrabutylammonium bromide in dimethyl sulphoxide or in the presence of an alkali metal hydride (for example sodium hydride), at a temperature between 20° C. and the boiling point of the reaction medium.

The derivatives Hal-Ri are commercially available or may be obtained from the corresponding alcohols by application or adaptation of the methods described by R. C. LAROCK, "Comprehensive Organic Transformations", Ed. VCH, page 353 (1989).

The compounds of formula (I) for which R represents a C($R_4$)$R_5$ radical, $R_4$ represents an alkyl or -alk-Het radical or a phenylalkyl radical in which the phenyl ring is optionally substituted and $R_5$ represents an alkyl (1–11C in an unbranched or branched chain), -alk-CN, -alk-Het, -alk-NR$_{10}$R$_{18}$, -alk-COOR$_{10}$, -alk-CO—NR$_{10}$R$_{18}$ or —COOR$_{10}$ radical or a phenylalkyl radical in which the phenyl ring is optionally substituted, or alternatively R represents a CH—$R_6$ radical and $R_6$ represents an —NR$_{14}$R$_{15}$ or -alk-NR$_{14}$R$_{15}$ radical, in which radicals $R_{14}$ and $R_{15}$, which may be identical or different, each represent an alkyl radical or alternatively $R_{14}$ represents a hydrogen atom and $R_{15}$ represents an alkyl, —COR$_{22}$ or —SO$_2$R$_{24}$ radical, $R_{22}$ represents an alkyl, cycloalkyl, —COOalk, -alk-COOR$_{10}$ or optionally substituted phenyl radical, a phenylalkyl radical in which the phenyl ring is optionally substituted or an —OR$_{17}$, -Het, -alk-Het or -alk-NR$_{10}$R$_{12}$ radical and $R_{24}$ represents an alkyl or phenyl radical, may be prepared by the action of a corresponding compound of formula (I) for which R represents a CH—$R_6$ radical and $R_6$ represents an alkyl or -alk-Het radical or a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, or R represents a CH—$R_6$ radical, $R_6$ represents an —NR$_{14}$Rl$_5$ or -alk-NR$_{14}$R$_{15}$ radical and $R_{14}$ and $R_{15}$ each represent a hydrogen atom, on a halide Hal-Rj for which Rj represents an alkyl (1–11C in an unbranched or branched chain), -alk-CN, -alk-Het, -alk-NR$_{10}$R$_{18}$, -alk-COOR$_{10}$, -alk-CO—NR$_{10}$R$_{18}$ or —COOR$_{10}$ radical, a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, or a —COR$_{22}$ or —SO$_2$R$_{24}$ radical, $R_{22}$ represents an alkyl, cycloalkyl, —COOalk or -alk-COOR$_{10}$ radical, a phenyl radical optionally substituted with one or more substituents chosen from halogen atoms and alkyl, alkoxy, nitro, amino, hydroxyl, -alk-NH$_2$, —COOR$_{10}$, cyano and -alk-COOR$_{10}$ radicals, a phenylalkyl radical in which the phenyl ring is optionally substituted with one or more substituents chosen from halogen atoms and alkyl, alkoxy, nitro, amino, hydroxyl, -alk-NH$_2$, —COOR$_1$O, cyano and -alk-COOR$_{10}$ radicals, or an —OR$_{171}$ -Het, -alk-Het or -alk-NR$_{10}$R$_{12}$ radical and $R_{24}$ represents an alkyl or phenyl radical, alk, Het and $R_{10}$ having the same meanings as in the formula (I), followed, for the compounds for which $R_5$ represents an -alk-COOR$_{10}$ or —COOR$_{10}$ radical in which radicals $R_{10}$ is a hydrogen atom, by a hydrolysis of the compound for which $R_5$ represents a —COOR$_{10}$ radical and $R_{10}$ is an alkyl radical.

This reaction is preferably performed in an inert solvent such as dimethyl sulphoxide, dimethylformamide, tetrahydrofuran or dioxane, in the presence of a base such as an alkali metal hydroxide (for example sodium hydroxide, potassium hydroxide), optionally in the presence of tetrabutylammonium bromide in dimethyl sulphoxide or in the presence of an alkali metal hydride (for example sodium hydride), at a temperature between 20° C. and the boiling point of the reaction medium. The hydrolysis is preferably performed by means of a base such as an alkali metal hydroxide (for example sodium hydroxide or potassium hydroxide), in a water/alcohol (for example ethanol) mixture, at a temperature of approximately 20 to 30° C.

The derivatives Hal-Rj are commercially available, or those for which Rj represents an -alk-CO—NR$_{10}$R$_{18}$ radical may be prepared by the action of an amine HNR$_{10}$R$_{18}$ on a derivative Hal-alk-CO-Hal in which Hal represents a halogen atom and alk represents an alkyl radical, in an inert solvent such as dimethylformamide, tetrahydrofuran or a chlorinated solvent, in the presence of an organic base such as a trialkylamine or pyridine, at a temperature between 0° C. and the boiling point of the reaction medium. The derivatives Hal-alk-CO-Hal are commercially available or may be obtained by halogenation of the corresponding carboxylic acids by means of a halogenating agent such as thionyl chloride, in an inert solvent such as 1,2- dichloroethane, at a temperature in the region of 60° C. The acids Hal-alk-COOH may be obtained by the action of an alkali metal cyanide on a derivative Hal-alk-Hal in which alk represents an alkyl radical and Hal represents a halogen atom, in a water/alcohol mixture, at a temperature between 0° C. and the boiling point of the reaction medium, followed by the action of a strong acid such as hydrochloric acid, in an aqueous medium, at a temperature between 0° C. and the boiling point of the reaction medium. The derivatives Hal-$COOR_{10}$ are commercially available or may be obtained by application or adaptation of the methods described in HOUBEN-WEYL, volume 8, page 102 (1952). Those for which Rj represents a —$COR_{22}$ radical may be obtained from the corresponding carboxylic acids by application or adaptation of the methods described by B. HELFERICH et al., Organic Synth., I, 147; R. ADAMS et al., Organic Synth., I, 304 and J. GASON, Organic Synth., III, 169, and those for which Rj represents an —$SO_2R_{24}$ radical may be obtained from the corresponding sulphonic acids by reacting a halogenated derivative of phosphorus (for example $PCl_5$, $POCl_3$) or thionyl chloride, in an aqueous phase or in an inert solvent (for example dichloromethane, at a temperature of between 20 and 40° C.

The compounds of formula (I) for which R represents a $C(R_4)R_5$ radical and $R_4$ and $R_5$, with the carbon atom to which they are attached, form a cycloalkyl radical may be prepared by the action of a corresponding compound of formula (I) for which R represents a CH—$R_6$ radical and $R_6$ represents a hydrogen atom on a derivative of formula Hal-alk-Hal in which Hal represents a halogen atom and alk represents an alkyl (2–5C) radical.

This reaction is preferably performed in an inert solvent such as dimethyl sulphoxide, dimethylformamide, tetrahydrofuran or dioxane, in the presence of a base such as an alkali metal hydroxide (for example sodium hydroxide, potassium hydroxide), optionally in the presence of tetrabutylammonium bromide in dimethyl sulphoxide or in the presence of an alkali metal hydride (for example sodium hydride), at a temperature between 20° C. and the boiling point of the reaction medium.

The compounds of formula (I) for which R represents a $C(R_4)R_5$ radical in which $R_5$ represents an —$NR_8R_9$ radical and $R_8$ and $R_9$ represent hydrogen atoms may be prepared by the action of a halide Hal-$R_4$ in which Hal represents a halogen atom and $R_4$ has the same meanings as in the formula (I) on a corresponding compound of formula (I) for which R represents a CH—$R_6$ radical, $R_6$ represents an —$NR_{14}R_{15}$ radical, $R_{14}$ represents a hydrogen atom, $R_{15}$ represents a —$COR_{22}$ radical and $R_{22}$ represents an alkyl (1C) radical, followed by a hydrolysis.

This reaction is generally performed in an inert solvent such as dimethyl sulphoxide, in the presence of an alkali metal hydride such as sodium hydride, at a temperature in the region of 20° C. The hydrolysis is generally performed by means of an inorganic acid such as hydrochloric acid, in an aqueous medium, at the boiling point of the reaction medium.

The compounds of formula (I) for which R represents a $C(R_4)R_5$ radical in which $R_5$ represents an —$NR_8R_9$ radical, $R_9$ represents a hydrogen atom and $R_8$ represents an alkyl, -alk-$COOR_{10}$, -alk-$NR_{10}R_{21}$ or -alk-Het radical or a phenylalkyl radical in which the phenyl ring is optionally substituted may be prepared by the action of a corresponding compound of formula (I) for which R represents a $C(R_4)R_5$ radical, $R_5$ represents an —$NR_8R_9$ radical and $R_8$ and $R_9$ represent hydrogen atoms on a halide Hal-$R_8$ in which $R_8$ has the same meanings as above.

This reaction is generally performed in an inert solvent such as dimethylformamide, in the presence of an alkali metal carbonate such as sodium or potassium carbonate or a trialkylamine such as triethylamine or pyridine, at a temperature between 0° C. and the boiling point of the reaction medium.

The halides Hal-$R_8$ are commercially available, or those for which $R_8$ represents an -alk-$NR_{10}R_{21}$ radical may be obtained by the action of the amine $HNR_{10}R_{21}$ in which $R_{10}$ and $R_{21}$ have the same meanings as in the formula (I) on a halide Hal-alk-Hal in which Hal represents a halogen atom and alk represents an alkyl radical, in an inert solvent such as dimethylformamide, in the presence of an acceptor for acid such as a nitrogenous base, at a temperature of between 0 and 25° C. Those for which $R_8$ represents an -alk-$COOR_{10}$ radical may be obtained by the action of a derivative Hal-alk-Hal in which Hal represents a halogen atom and alk represents an alkyl radical on an alkali metal cyanide (sodium or potassium cyanide), in a water/alcohol mixture, at a temperature between 0° C. and the boiling point of the reaction medium, followed by the action of a strong acid such as HCl, optionally in the presence of an alcohol, at a temperature between 0° C. and the boiling point of the reaction medium.

The compounds of formula (I) for which R represents a $C(R_4)R_5$ radical in which $R_5$ represents an —$NR_8R_9$ radical, $R_8$ has the same meanings as in the formula (I) and $R_9$ represents an alkyl radical may also be prepared by the action of a corresponding compound of formula (I) for which R represents a $C(R_4)R_5$ radical, $R_5$ represents an —$NR_8R_9$ radical, $R_8$ has the same meanings as in the formula (I) and $R_9$ represents a hydrogen atom on a derivative of formula Hal-$R_9$ in which Hal represents a halogen atom and $R_9$ represents an alkyl radical.

This reaction is performed in an inert solvent such as dimethylformamide, in the presence of an acceptor for acid such as a nitrogenous organic base (pyridine or trialkylamine such as triethylamine), at a temperature between 0° C. and the boiling point of the reaction medium.

The derivatives Hal-$R_9$ are commercially available or may be obtained by application or adaptation of the methods described by C. LAROCK, "Comprehensive Organic Transformations", Ed. VCH, pages 345 and 353 (1989).

The compounds of formula (I) for which R represents a $C(R_4)R_5$ radical in which $R_5$ represents an -alk-$COOR_{10}$ radical may be prepared by the action of a corresponding compound of formula (I) for which R represents a CH—$R_6$ radical, $R_6$ represents an -alk-$COOR_{10}$ radical and $R_{10}$ has the same meanings as in the formula (I) on a halide Hal-$R_4$ in which $R_4$ has the same meanings as in the formula (I).

This reaction is performed in an inert solvent such as dimethylformamide, in the presence of an alkali metal hydride such as sodium or potassium hydride, at a temperature in the region of 20° C.

The compounds of formula (I) for which R represents a $C(R_4)R_5$ radical in which $R_5$ represents an -alk(2-6C)OH radical may be prepared by the action of $(COCl)_2$ on a corresponding compound of formula (I) for which R represents a $C(R_4)R_5$ radical in which $R_5$ represents an -alk-$COOR_{10}$ radical and $R_{10}$ represents a hydrogen atom, followed by a reduction.

This reaction is performed in an inert solvent such as dioxane. The reduction is preferably performed by means of sodium borohydride, in an inert solvent such as dimethylformamide, at a temperature of between 10 and 20° C.

The compounds of formula (I) for which R represents a $C(R_4)R_5$ radical in which $R_5$ represents an -alk(1C)OH radical may be prepared by the action of trimethylsilane chloride on a corresponding compound of formula (I) for which R represents a CH—$R_6$ radical and $R_6$ represents an alkyl or -alk-Het radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, and then of trioxane.

This reaction is generally performed in an inert solvent such as dimethylformamide, in the presence of sodium hydride, followed by reaction with trioxane at a temperature of between 0 and 25° C.

The compounds of formula (I) for which R represents a $C(R_4)R_5$ radical in which $R_5$ represents an —NH—CHO radical, or R represents a CH—$R_6$ radical and $R_6$ represents an —NH—CHO radical, may be prepared by the action of a corresponding compound of formula (I) for which R represents a $C(R_4)R_5$ radical in which $R_5$ represents an —$NR_8R_9$ radical, $R_8$ and $R_9$ being hydrogen atoms, or R represents a CH—$R_6$ radical, $R_6$ represents an —$NR_{14}R_{15}$ radical and $R_{14}$ and $R_{15}$ represent hydrogen atoms, on $CH_3COOCHO$.

This reaction is preferably performed in an inert solvent such as formic acid, in the presence of sodium acetate, at a temperature in the region of 20° C.

The compounds of formula (I) for which R represents a $C(R_4)R_5$ radical in which $R_5$ represents an —NH—$COOR_{17}$, —NH—CO-Het, —NH—CO-alk-$COOR_{10}$ or —NH—CO-alk—$NR_{10}R_{18}$ radical, an —NH—CO—Ar radical in which Ar is optionally substituted, an —NH—CO-alk-Ar radical in which Ar is optionally substituted or an —NH-$SO_2$—$R_{24}$, —NH—CO-alk-Het, —NH—CO-alk or —NH—CO-cycloalkyl radical, or R represents CH—$R_6$, $R_6$ represents an —$NR_{14}R_{15}$ radical, $R_{14}$ represents a hydrogen atom, $R_{15}$ represents a —$COR_{22}$ radical and $R_{22}$ represents an —$OR_{17}$, -Het, -alk-$COOR_{10}$ or -alk-$NR_{10}R_{12}$ radical, an -alk-Ar radical in which Ar is optionally substituted, an -alk-Het radical or a phenyl radical optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, may be prepared by the action of a corresponding compound of formula (I) for which R represents a $C(R_4)R_5$ radical, $R_5$ represents an —$NR_8R_9$ radical and $R_8$ and $R_9$ represent hydrogen atoms, or R represents a CH—$R_6$ radical, $R_6$ represents an —$NR_{14}R_{15}$ radical, $R_{14}$ represents a hydrogen atom and $R_{15}$ represents a hydrogen atom, on a derivative Hal-Rk in which Hal represents a halogen atom and Rk represents a —$COOR_{17}$, —CO-Het, —CO-alk-$COOR_{10}$, —CO-alk-$NR_{10}R_{18}$ or —CO-alk-$NR_{10}R_{12}$ radical, a —CO-alk-Ar radical in which Ar is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, a —CO-alk-Het, —$SO_2$—$R_{24}$ or —CO-alk-Het radical, a —CO—Ar radical in which Ar is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, or a —CO-alk or —CO—cycloalkyl radical, $R_7$, $R_{10}$, $R_{12}$, $R_{17}$, $R_{18}$, $R_{24}$, Het, Ar and alk having the same meanings as in the formula (I).

This reaction is generally performed in an inert solvent such as dimethylformamide or dimethyl sulphoxide, in the presence of an acceptor for acid such as a trialkylamine (for example triethylamine) or an alkali metal hydride (for example sodium hydride) at a temperature in the region of 20° C.

The derivatives Hal-Rk are commercially available or those for which Rk represents a —CO-Het, —CO-alk-Het, —CO-cycloalkyl, —CO-alk-$COOR_{10}$ or —CO-alk-$NR_{10}R_{18}$ radical or a —CO-alk-Ar radical in which Ar is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals may be obtained from the corresponding carboxylic acids by the action of a phosphorus halide (for example $PCl_5$ or $POCl_3$), preferably in the phosphorus halide, optionally in the presence of an inert solvent such as dichloromethane, at a temperature between 20° C. and the boiling point of the reaction medium, or by application or adaptation of the methods described by R. HELPER et al., Organic Synth., I, 147 and R. ADAMS et al., Organic Synth., I, 394 and J. CASON, Organic Synth., III, 169.

The compounds of formula (I) for which R represents a $C(R_4)R_5$ radical in which $R_5$ represents an —NH—CO-Het, —NH—CO-alk-$COOR_{10}$ or —NH—CO-alk-$NR_{10}R_{18}$ radical, an —NH—CO—Ar radical in which Ar is optionally substituted, an —NH—CO-alk-Ar radical in which Ar is optionally substituted, or an —NH—CO-alk-Het, —NH—CO-alk or —NH—CO-cycloalkyl radical, or R represents a CH—$R_6$ radical, $R_6$ represents an —$NR_{14}R_{15}$ radical, $R_{14}$ represents a hydrogen atom, $R_{15}$ represents a —$COR_{22}$ radical and $R_{22}$ represents a -Het, -alk-$COOR_{10}$ or -alk-$NR_{10}R_{12}$ radical, a phenylalkyl radical in which the phenyl is optionally substituted, an -alk-Het radical or an optionally substituted phenyl radical, may also be prepared by the action of a compound of formula (I) in which R represents a $C(R_4)R_5$ radical, $R_5$ represents an —$NR_8R_9$ radical and $R_8$ and $R_9$ represent hydrogen atoms, or R represents a CH—$R_6$ radical, $R_6$ represents an —$NR_{14}R_{15}$ radical, $R_{14}$ represents a hydrogen atom and $R_{15}$ represents a hydrogen atom, on a derivative HO—RI in which RI represents a —CO-Het, —CO-alk-$COOR_{10}$, —CO-alk-$NR_{10}R_{18}$ or —CO-alk-$NRIOR_{12}$ radical, a —CO-alk-Ar radical in which Ar is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, a —CO-alk-Het radical, a —CO—Ar radical in which Ar is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, or a —CO-alk or —CO-cycloalkyl radical, $R_{10}$, $R_{12}$, $R_{18}$, Het, Ar and alk having the same meanings as in the formula (I).

This reaction is generally performed in an inert solvent such as dimethylformamide, in the presence of hydroxybenzotriazole, 1-(3-dimethylaminopropyl)-3-ethylcabodiimide and an organic base such as a trialkylamine (for example triethylamine), at a temperature of between 0° C. and 5° C.

The compounds of formula (I) for which R represents a $C(R_4)R_5$ radical in which $R_5$ represents a 1-pyrrolyl radical optionally substituted with a —$COOR_{10}$ radical, or R represents a CH—$R_6$ radical and $R_6$ represents a 1-pyrrolyl radical optionally substituted with a —$COOR_{10}$ radical, may be prepared by the action of a corresponding compound of formula (I) for which R represents a $C(R_4)R_5$ radical in which $R_5$ represents an —$NR_8R_9$ radical and $R_8$ and $R_9$ represent hydrogen atoms, or R represents a CH—$R_6$ radical, $R_6$ represents an —$NR_{14}R_{15}$ radical and $R_{14}$ and $R_{15}$ represent hydrogen atoms, on a derivative of formula:

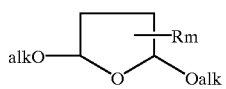

(V)

in which alk represents an alkyl radical, Rm represents a hydrogen atom or a —COOR$_{10}$ radical and R$_{10}$ has the same meanings as in the formula (I).

This reaction is generally performed in an inert solvent such as acetic acid, at the boiling point of the reaction medium, optionally in the presence of an acceptor for acids such as sodium acetate.

The derivatives of formula (V) may be obtained by application or adaptation of the methods described by J. FAKSTORP et al., J. Am. Chem. Soc., 72, 869 (1950), N. CLAUSON-KAAS et al., Acta Chem. Scan., 6, 551 (1952) and STIBOR et al., Collect. Czech. Chem. Commun., 47 (12), 3261 (1992).

The compounds of formula (I) for which R represents a C(R$_4$)R$_5$ radical in which R$_5$ represents an —NH—CO—NH-alk-Ar radical in which Ar is optionally substituted, an —NH—CO—NH-Het or —NH—CO—NH-alk-Het radical, an —NH—CO—NH—Ar radical in which Ar is optionally substituted, or an —NH—CO—NH-alk or —NH—CO—NH2 radical, or R represents a CH—R$_6$ radical and R$_6$ represents an —NR$_{14}$R$_{15}$ or -alk-NR$_{14}$R$_{15}$ radical in which radicals R$_{14}$ represents a hydrogen atom, R$_{15}$ represents a —COR$_{22}$ or —CSR$_{23}$ radical, R$_{22}$ represents an —NH-alk or —NH$_2$ radical, an —NH—Ar radical in which Ar is optionally substituted, an —NH-alk-Ar radical in which Ar is optionally substituted, or an —NH-alk-Het or —NH-Het radical and R$_{23}$ represents an —NH-alk, —NH$_2$, —NH—Ar or —NH-Het radical, may be prepared by the action of a corresponding compound of formula (I) for which R represents a C(R$_4$)R$_5$ radical, R$_5$ represents an —NR$_8$R$_9$ radical and R$_8$ and R$_9$ represent hydrogen atoms, or R represents a CH—R$_6$ radical and R$_6$ represents an —NR$_{14}$R$_{15}$ or -alk-NR$_{14}$R$_{15}$ radical in which radicals R$_{14}$ and R$_{15}$ each represent a hydrogen atom, on a derivative Rn=C=N—Ro in which Rn represents a trimethylsilyl, alkyl or -Het radical, a phenylalkyl radical in which the phenyl is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, an -alk-Het radical or a phenyl radical optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals in which radicals R$_{10}$ alk, Ar and Het have the same meanings as in the formula (I) and Ro represents an oxygen or sulphur atom, optionally followed by a hydrolysis.

This reaction is generally performed in an inert solvent such as dimethylformamide, tetrahydrofuran or dioxane, at a temperature between 20° C. and the boiling point of the reaction medium. For the compounds for which R$_5$ represents an —NH—CO—NH$_2$ radical or R$_{22}$ and R$_{23}$ are NH$_2$ radicals, this reaction is followed by a hydrolysis of the silyl derivative previously obtained by means of an aqueous solution, at a temperature of between 20 and 50° C.

The derivatives Rn—N=C=Ro may be obtained from the corresponding primary amines by the action of phosgene or thiophosgene, by application or adaptation of the methods described by R. L. SHRINER et al., Organic Synth., II, 453 and G. M. DYSON, Organic Synth., I, 165; R. J. SLOCOMPIE et al., J. Am. Chem. Soc., 72, 1888 (1950) and S. PATAI, "The chemistry of cyanates and their thio derivatives", Ed. John Wiley and Sons, pages 619 and 819 (1977).

The corresponding primary amines are commercially available, or those for which Rp represents an optionally substituted phenyl or Het radical may be obtained by application or adaptation of the methods described by B. A. TERTOV et al., Khim. Geterotsikl. Soedin, II, 1552 (1972) and R. C. LAROCK, "Comprehensive Organic Transformations", Ed. VCH, page 399, which consists in reacting the organolithium or organomagnesium derivative of the heterocycle or of the optionally substituted benzene with PhN$_3$, in the presence of acetic acid, NH$_2$OCH$_3$, (PhO)$_2$PON$_3$ or N$_3$CH$_2$Si (CH$_3$)$_3$. The organolithium or organomagnesium derivatives may be obtained by application or adaptation of the methods described by D. L. COMINS et al., J. Org. Chem., 52, 104 (1987); N. FURUKANA et al., Tetrahedron Lett., 28 (47), 5845 (1987); A. R. KATRITZKY et al., Org. Prep. Procedure Int., 20 (6), 585 (1988), A. J. CLARKE et al., Tetrahedron Lett., 27, 2373 (1974) and A. W. GSCHWEN et al., Organic Reaction, 26, 1 (1979). The amines for which Rp represents an -alk-Het radical or an -alk-Ar radical in which Ar is optionally substituted are commercially available or are obtained from the corresponding halides by the action of NaN(SiCH$_3$)$_3$ or of the potassium salt of phthalimide, in an inert solvent such as dimethylformamide, in the presence of an organic base such as a trialkylamine or pyridine, at a temperature between 0° C. and the boiling point of the reaction medium, followed by a hydrolysis, either in an acid medium (for example HCl) at a temperature between 20° C. and the boiling point of the reaction medium, or by means of hydrazine, in a lower aliphatic alcohol, at the boiling point of the reaction medium. The derivatives H$_2$N-alk-Ar in which Ar is optionally substituted may also be obtained by application or adaptation of the methods described by J. F. KING et al., J. Am. Chem. Soc., 114, 3028 (1992); B. M. ADGER et al., Tetrahedron Lett., 25 (45), 5219 (1984); R. SCARPATI et al., Gazz. Chim. Ital., 97 (5), 654 (1967).

The compounds of formula (I) for which R represents a CH—R$_6$ radical in which R$_6$ represents a hydroxyl radical may be prepared by reducing a corresponding compound of formula (I) for which R represents a C=R$_7$ radical and R$_7$ represents an oxygen atom.

This reaction is preferably performed in an inert solvent such as an alcohol (for example methanol, ethanol), in the presence of sodium borohydride, at a temperature of between 15 and 40° C.

The compounds of formula (I) for which R represents a CH—R$_6$ radical in which R$_6$ represents an alkyl (2–11C) radical, a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, or an -alk-COOR$_{10}$ or -alk-Het radical may be prepared by hydrogenation of a derivative of formula:

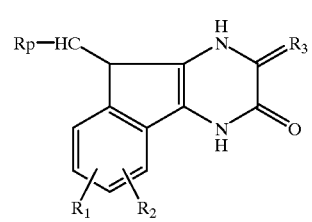

(VI)

in which R$_1$, R$_2$ and R$_3$ have the same meanings as in the formula (I), Rp represents an unbranched- or branched-chain alkyl radical containing 1 to 10 carbon atoms, a phenyl radical optionally substituted with one or more substituents chosen from halogen atoms and alkyl, alkoxy, nitro, amino, hydroxyl, cyano, -alk-NH$_2$, —COOR$_{10}$ and -alk-COOR$_{10}$ radicals, a phenylalkyl (1–5C) radical in which the phenyl ring is optionally substituted with one or more substituents chosen from halogen atoms and alkyl, alkoxy, nitro, amino, hydroxyl, cyano, -alk-$NH_2$, —$COOR_{10}$ and -alk-$COOR_{10}$ radicals, or a —$COOR_{10}$, -alk(1–5C)—$COOR_{10}$, -Het or -alk(1–5C)-Het radical in which radicals alk, Het and $R_{10}$ have the same meanings as in the formula (I) and alk represents an alkyl radical, optionally followed by a saponification of the compounds for which $R_6$ is an -alk-$COOR_{10}$ radical and $R_{10}$ is an alkyl radical, to obtain the compounds for which $R_6$ is an -alk-$COOR_{10}$ radical and $R_{10}$ is a hydrogen atom.

This reduction is performed by means of hydrogen at a pressure of 1 to 20 bar, in the presence of a hydrogenation catalyst such as palladinized charcoal, palladium hydroxide or palladium (N. RICO et al., Nouveau Journal de Chimie, 10, 1, 25 (1986)), in an inert solvent such as dimethylformamide, acetic acid, ethyl acetate, an alcohol (for example methanol or ethanol) or a mixture of these solvents, at a temperature of between 20 and 60° C., or by adaptation of the method of L. M. STRAWN et al., J. Med. Chem., 32, 2104 (1989), which consists in reacting the ethylenic derivative with hydroxylamine sulphate and $H_2NOSO_3H$, in an aqueous medium, at a pH of between 6 and 7, at a temperature of 10° C. The saponification is performed by any known method, and preferably by means of an acid such as hydrochloric acid, in an alcohol such as ethanol, at a temperature of 20 to 60° C., or by means of trifluoroacetic acid at a temperature in the region of 20 to 60° C.

The derivatives of formula (VI) for which Rp represents an unbranched- or branched-chain alkyl radical containing 5 to 10 carbon atoms may be prepared as described above for their homologues (compounds of formula (I) for which R represents a C=$R_7$ radical, $R_7$ represents a —CH—$R_{19}$ radical and $R_{19}$ represents an alkyl radical).

The derivatives of formula (VI) for which Rp represents a —$COOR_{10}$ radical in which Rio represents an alkyl radical may be obtained by the action of a corresponding compound of formula (I) for which R represents a CH—$R_6$ radical and $R_6$ represents a hydrogen atom on an alkyl glyoxalate. This reaction is performed in an inert solvent such as dimethyl sulphoxide, in the presence of an alkali metal hydride (for example sodium or potassium hydride), at a temperature in the region of 20° C.

The compounds of formula (I) for which R represents a CH—$R_6$ radical in which $R_6$ represents a methyl radical may also be prepared by reduction of the corresponding compounds of formula (I) for which R represents a C=$R_7$ radical, $R_7$ represents a CH—$R_{19}$ radical and $R_{19}$ represents a hydroxyl or —$NR_{25}R_{26}$ radical.

This reduction is generally performed by means of hydrogen, under a pressure of 1 to 50 bar, in an inert solvent such as dimethylformamide, acetic acid, ethyl acetate, an alcohol (for example methanol, ethanol) or a mixture of these solvents, in the presence of a hydrogenation catalyst such as palladinized charcoal or palladium hydroxide, at a temperature of between 20° C. and 60° C.

The compounds of formula (I) for which R represents a CH—$R_6$ radical and $R_6$ represents an -alk(1C)—OH radical may be prepared by reduction of the corresponding compounds of formula (I) for which R represents a C=$R_7$ radical, $R_7$ represents a CH—$R_{19}$ radical and $R_{19}$ represents a hydroxyl radical.

This reduction is generally performed using reducing agents such as sodium borohydride, in an inert solvent such as an alcohol (for example methanol, ethanol), at a temperature in the region of 20° C.

The compounds of formula (I) for which R represents a CH—$R_6$ radical and $R_6$ represents an -alk(2–6C)—OH radical may be prepared by reduction of a derivative of formula (VI) in which $R_1$, $R_2$ and $R_3$ have the same meanings as in the formula (I) and Rp represents an -alk(1–5C)—O—$CH_2$—Ar radical, alk and Ar having the same meanings as in the formula (I).

This reduction is preferably performed by means of hydrogen, under a pressure of 1 to 50 bar, in the presence of a catalyst such as palladinized charcoal or palladium hydroxide, in an inert solvent such as dimethylformamide, acetic acid, an alcohol or ethyl acetate, at a temperature of between 20 and 60° C.

The derivatives of formula (VI) for which Rp represents an -alk(1–5C)—O—$CH_2$—Ar radical may be obtained by the action of a corresponding compound of formula (I) for which R represents a CH—$R_6$ radical and $R_6$ represents a hydrogen atom on an aldehyde OHC-alk(1–5C)—O—$CH_2$—Ar.

This reaction is performed under the same conditions as those mentioned above for the preparation of the compounds of formula (I) for which R represents a C=$R_7$ radical, $R_7$ represents a CH—$R_{19}$ radical and $R_{19}$ represents an alkyl radical.

The derivatives OHC-alk(1–5C)—O—$CH_2$—Ar may be obtained by application or adaptation of the methods described by P. SCHORIGIN et al., Chem. Ber., 68, 838 (1935) and A. GAIFFE et al., C. R. Acad. Sc. Paris, Ser. C. 266, 1379 (1968).

The compounds of formula (I) for which R represents a CH—$R_6$ radical in which $R_6$ represents an —$NR14R_{15}$ radical and $R_{14}$ and $R_{15}$ each represent a hydrogen atom may be prepared by hydrolysis of a corresponding compound of formula (I) for which R represents a CH—$R_6$ radical in which $R_6$ represents an —$NR_{14}R_{15}$ radical, $R_{14}$ represents a hydrogen atom, $R_{15}$ represents a —$COR_{22}$ radical and $R_{22}$ represents an alkyl radical.

This hydrolysis is generally performed by means of an acid such as hydrochloric acid, in an aqueous medium, at the boiling point of the reaction medium.

The compounds of formula (I) for which R represents a CH—$R_6$ radical in which $R_6$ represents an —$NR_{14}R_{15}$ radical, $R_{14}$ represents a hydrogen atom, $R_{15}$ represents a —$COR_{22}$ radical and $R_{22}$ represents an alkyl radical may be prepared by the action of a reducing agent on a corresponding compound of formula (I) for which R represents a C=$R_7$ radical and $R_7$ represents an NOH radical, followed by treatment with an anhydride $(RqCO)_2O$ for which Rq represents an alkyl radical.

This reaction is generally performed at a temperature of between 50 and 100° C. As a reducing agent, zinc is preferably used.

The compounds of formula (I) for which R represents a CH—$R_6$ radical and $R_6$ represents an —$NR_{14}R_{15}$ or -alk-$NR_{14}R_{15}$ radical in which radicals $R_{14}$ and $R_{15}$, which may be identical or different, each represent an alkyl radical may be prepared by the action of a corresponding compound of formula (I) for which R represents a CH—$R_6$ radical, $R_6$ represents an —$NR_{14}R_{15}$ or -alk-$NR_{14}R_{15}$ radical, $R_{14}$ represents a hydrogen atom and $R_{15}$ represents an alkyl radical on a halide of formula Hal-Rr in which Rr represents an alkyl radical.

This reaction is preferably performed in an inert solvent such as dimethylformamide, tetrahydrofuran or dimethyl sulphoxide, in the presence of a base such as a tertiary amine (for example triethylamine) or aromatic amine (for example pyridine) or an inorganic base such as an alkali metal hydroxide (for example sodium hydroxide, potassium hydroxide), at a temperature between 20° C. and the boiling point of the reaction medium.

The compounds of formula (I) for which R represents a CH—$R_6$ radical and $R_6$ represents an —$NR_{14}R_{15}$ or -alk-$NR_{14}R_{15}$ radical in which radicals $R_{14}$ represents a hydrogen atom, $R_{15}$ represents a —$COR_{22}$ radical and $R_{22}$ represents an -alk-$NR_{10}R_{12}$ radical in which $R_{10}$ and $R_{12}$ represent hydrogen atoms and alk contains 1 carbon atom may be prepared by the action of a corresponding compound of formula (I) for which R represents a CH—$R_6$ radical, $R_6$ represents an —$NR_{14}R_{15}$ or -alk-$NR_{14}R_{15}$ radical and $R_{14}$ and $R_{15}$ each represent a hydrogen atom on an acid HOOC—$CH_2$—NH—Rs in which Rs represents a group protecting the amine function, such as tert-butoxycarbonyl, followed by a hydrolysis.

This reaction is preferably performed in an inert solvent such as dimethylformamide, in the presence of hydroxybenzotriazole, 1-(3-dimethylaminopropyl)-3-ethylcarbodiimide and an organic base such as a trialkylamine (for example triethylamine), at a temperature of between 0 and 5° C. The hydrolysis is generally performed by means of trifluoroacetic acid at a temperature in the region of 20° C.

The compounds of formula (I) in which R represents a CH—$R_6$ radical, $R_6$ represents an -alk-$NR_{14}R_{15}$ radical and $R_{14}$ and $R_{15}$ each represent a hydrogen atom may be prepared by the action of bromine and sodium hydroxide on a compound of formula (I) for which R represents a CH—$R_6$ radical, $R_6$ represents an -alk-CO—$NR_{10}R_{18}$ radical and $R_{10}$ and $R_{18}$ represent hydrogen atoms.

This reaction is generally performed in an aqueous medium at a temperature of between 20 and 70° C.

The compounds of formula (I) for which R represents a CH—$R_6$ radical and $R_6$ represents an -alk-CO—$NR_{10}R_{18}$ radical may be prepared by the action of a corresponding compound of formula (I) for which R represents a CH—$R_6$ radical and $R_6$ represents an -alk-COOR$_{10}$ radical on an amine $HNR_{10}R_{18}$ in which $R_{10}$ and $R_{18}$ have the same meanings as in the formula (I).

When the acid is employed, the reaction is performed in the presence of a condensing agent used in peptide chemistry, such as a carbodiimide (for example N,N'-dicyclohexylcarbodiimide) or N,N'-carbonyldiimidazole, in an inert solvent such as an ether (for example tetrahydrofuran, dioxane), an amide (dimethylformamide) or a chlorinated solvent (for example methylene chloride, 1,2-dichloroethane, chloroform), at a temperature between 0° C. and the refluxing temperature of the reaction mixture. When an ester is employed, the reaction is then performed either in an organic medium, optionally in the presence of an acceptor for acid such as a nitrogenous organic base (for example trialkylamine, pyridine, 1,8-diazabicyclo[5.4.0]undec-7-ene or 1,5-diazabicyclo-[4.3.0]non-5-ene), in a solvent as is mentioned above, or a mixture of these solvents, at a temperature between 0° C. and the refluxing temperature of the reaction mixture, or in a two-phase aqueous-organic medium in the presence of an alkali metal base or alkaline-earth metal base (sodium hydroxide, potassium hydroxide) or an alkali metal carbonate or bicarbonate or alkaline-earth metal carbonate or bicarbonate, at a temperature of between 0 and 40° C.

The amines $HNR_{10}R_{18}$ are commercially available or may be obtained from the corresponding halides by application or adaptation of the methods described by R. C. LAROCK, "Comprehensive Organic Transformations", Ed. VCH, page 397 (1989).

The compounds of formula (I) for which R represents a CH—$R_6$ radical, $R_6$ represents an -alk(1C)—CO—$NR_{10}R_{18}$ radical and $R_{10}$ and $R_{18}$ represent hydrogen atoms may also be prepared by hydrogenation of a derivative of formula (VI) in which $R_1$, $R_2$ and $R_3$ have the same meanings as in the formula (I) and Rp represents a —$CONH_2$ radical.

This reaction is generally performed either by means of hydrogen, in an inert solvent such as dimethylformamide, in the presence of a hydrogenation catalyst such as palladinized charcoal or palladium, at a temperature in the region of 20 to 30° C., or by adaptation of the method of L. M. STRAWN et al., J. Med. Chem., 32, 2104 (1989), which consists in reacting the ethylenic derivative with hydroxylamine sulphate and $H_2NOSO_3H$, in an aqueous medium, at a pH of between 6 and 7, at a temperature of 10° C.

The derivatives of formula (VI) in which $R_1$, $R_2$ and $R_3$ have the same meanings as in the formula (I) and Rp represents a —$CONH_2$ radical may be obtained by the action of ammonia on a corresponding compound of formula (VI) for which Rp represents a —COOR$_{10}$ radical in which $R_{10}$ represents an alkyl radical, under the conditions described by D. I. MOWRY et al., Organic Synth., IV, 486 and J. KLEINBERG et al., Organic Synth., IV, 516.

The compounds of formula (I) for which R represents a CH—$R_6$ radical and $R_6$ represents an —$Rl_6$—COOR$_{10}$ radical may be prepared by the action of a corresponding compound of formula (I) for which R represents a CH—$R_6$ radical and $R_6$ represents a hydrogen atom on a derivative of formula OHC-alk(0–5C)—COOR$_{10}$ in which $R_{10}$ has the same meanings as in the formula (I).

This reaction is preferably performed in an inert solvent such as dimethyl sulphoxide, in the presence of an alkali metal hydride such as sodium hydride, at a temperature in the region of 20° C.

The derivatives of formula OHC-alk(0–5C) —COOR$_{10}$ may be obtained by application or adaptation of the method described by L. A. CARPINO, J. Org. Chem., 29, 2820 (1964).

The compounds of formula (I) for which R represents a CH—$R_6$ radical and $R_6$ represents a —CO—COOR$_{10}$ radical may be prepared by oxidation of a corresponding compound of formula (I) for which R represents a CH—$R_6$ radical, $R_6$ represents an —$Rl_6$—COOR$_{10}$ radical in which $R_{10}$ represents a hydrogen atom and $R_{16}$ represents a —CHOH— radical, optionally followed by an esterification.

This oxidation is preferably performed by means of potassium permanganate, in 3N sodium hydroxide solution, at a temperature in the region of –3° C., or by means of platinum on charcoal, in 2N sodium hydroxide solution, at a temperature of 70° C. The esterification is preferably performed by means of an alcohol, in the presence of an acid such as hydrochloric or sulphuric acid, at the boiling point of the reaction medium.

The compounds of formula (I) for which R represents a CH—$R_6$ radical and $R_6$ represents a —COOalk radical may be prepared by the action of an inorganic acid on a derivative of formula:

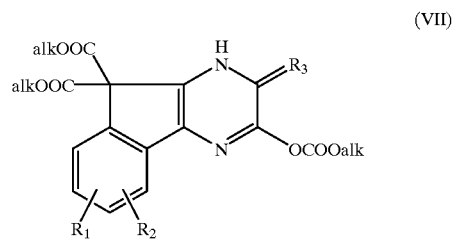

(VII)

in which $R_1$, $R_2$ and $R_3$ have the same meanings as in the formula (I) and alk represents an alkyl radical.

This reaction is generally performed in an inert solvent such as tetrahydrofuran at a temperature of 0° C. As an inorganic acid, hydrochloric acid in 1N aqueous solution is preferably used.

The derivatives of formula (VII) may be obtained by the action of a corresponding compound of formula (I) for which R represents a CH—R$_6$ radical and R$_6$ represents a hydrogen atom on a halide Hal-COOalk in which alk represents an alkyl radical.

This reaction is generally performed in an inert solvent such as dioxane, in the presence of an alkali metal hydride (for example sodium), at a temperature between 20° C. and the boiling point of the reaction medium.

The derivatives Hal-COOalk are commercially available or may be obtained by application or adaptation of the methods described in HOUBEN-WEYL, volume 8, page 108 (1952).

The compounds of formula (I) for which R$_1$ and possibly R$_2$ represent an —NH—CO—NR$_{11}$R$_{12}$ or —NH—CS—NR$_{11}$R$_{12}$ radical and R$_{12}$ represents a hydrogen atom may also be prepared by the action of a corresponding compound of formula (I) for which R$_1$ represents an amino radical on a derivative Rx=C=N=Ry in which Rx represents an oxygen or sulphur atom and Ry represents a trimethylsilyl, alkyl, alkoxy, -alk-COOR$_{10}$, -alk-Het or -alkNR$_{12}$R$_{10}$ radical, a phenylalkyl radical in which the phenyl is optionally substituted with one or more substituents chosen from halogen atoms and alkyl, alkoxy, nitro, amino, hydroxyl, cyano, -alk-NH$_2$, —COOR$_7$ and -alk-COOR$_7$ radicals, a phenyl radical optionally substituted with one or more substituents chosen from halogen atoms and alkyl, alkoxy, nitro, amino, hydroxyl, cyano, -alk-NH$_2$, —COOR$_7$ and -alk-COOR$_7$ radicals, or a Het radical in which radicals alk, Het, R$_7$, R$_9$, R$_{10}$ and R$_{12}$ have the same meanings as in the formula (I).

This reaction is generally performed in an inert solvent such as dimethylformamide, tetrahydrofuran or dioxane, at a temperature between 20° C. and the boiling point of the reaction medium, followed by a hydrolysis of the silyl derivative to obtain the compound for which R$_{12}$ represents a hydrogen atom, by means of an aqueous solution, at a temperature of between 20 and 50° C.

For a person skilled in the art, it is understood that, to carry out the processes described above according to the invention, it may be necessary to introduce groups protecting the amino, hydroxyl and carboxyl functions in order to avoid side reactions. These groups are the ones which make it possible for them to be removed without affecting the remainder of the molecule. As examples of groups protecting the amino function, tert-butyl or methyl carbamate, which can be regenerated by means of iodotrimethylsilane, may be mentioned. As examples of groups protecting the hydroxyl function, triethylsilyl and benzyl may be mentioned. As groups protecting the carboxyl functions, esters (for example methoxymethyl ester, tetrahydropyranyl ester, benzyl ester), oxazoles and 2-alkyl-1,3-oxazolines may be mentioned. Other usable protective groups are described by W. GREENE et al., Protecting Groups in Organic Synthesis, second edition, 1991, John Wiley & Sons.

The compounds of formula (I) may be purified by the usual known methods, for example by crystallization, chromatography or extraction.

The enantiomers of the compounds of formula (I) for which R represents a C(R$_4$)R$_5$ or CH—R$_6$ radical may be obtained by resolution of the racemates, for example by chiral-column chromatography according to W. H. PIRCKLE et al., asymmetric synthesis, vol. 1, Academic Press (1983) or by synthesis from chiral precursors.

The diastereoisomers of the compounds of formula (I) for which R represents a C(R$_4$)R$_5$ or CH—R$_6$ radical containing one or more chiral carbons, and the different E and Z isomers of the compounds of formula (I), may be separated by the usual known methods, for example by crystallization or chromatography.

The compounds of formula (I) containing a basic residue can be optionally converted to addition salts with an inorganic or organic acid, by the action of such an acid in an organic solvent such as an alcohol, a ketone, an ether or a chlorinated solvent.

The compounds of formula (I) containing an acidic residue can optionally be converted to metal salts or to addition salts with nitrogenous bases according to methods known per se. These salts may be obtained by the action of a metal base (for example an alkali metal or alkaline-earth metal base), ammonia, an amine or an amine salt on a compound of formula (I), in a solvent. The salt formed is separated by the usual methods.

These salts also form part of the invention.

As examples of pharmaceutically acceptable salts, there may be mentioned the addition salts with inorganic or organic acids (such as acetate, propionate, succinate, benzoate, fumarate, maleate, oxalate, methanesulphonate, isethionate, theophyllineacetate, salicylate, methylenebis(β-hydroxynaphthoate, hydrochloride, sulphate, nitrate and phosphate), salts with alkali metals (sodium, potassium, lithium) or with alkaline-earth metals (calcium, magnesium), the ammonium salt and the salts of nitrogenous bases (ethanolamine, trimethylamine, methylamine, benzylamine, N-benzyl-β-phenethylamine, choline, arginine, leucine, lysine, N-methylglucamine).

The compounds of formula (I) possess advantageous pharmacological properties. These compounds are antagonists of the α-amino-3-hydroxy-5-methyl-4-isoxazolepropionic acid (AMPA) receptor, also known by the name quisqualate receptor.

Moreover, the compounds of formula (I) are noncompetitive antagonists of the N-methyl-D-aspartate (NMDA) receptor and, more especially, they are ligands for the glycine-modulating sites of the NMDA receptor.

These compounds are hence useful for treating or preventing all ischaemias (such as focal or global ischaemia) following cerebrovascular accidents, cardiac arrest, arterial hypotension, heart or lung surgery or severe hypoglycaemia. They are also useful in the treatment of the effects due to anoxia, either perinatal or following drowning or cerebrospinal lesions. These compounds may also be used for treating or preventing the progression of neurodegenerative diseases, Huntington's chorea, Alzheimer's disease, amyotrophic lateral sclerosis, olivopontocerebellar atrophy and Parkinson's disease. These compounds may also be used for epileptogenic and/or convulsive manifestations, for the treatment of cerebral or spinal trauma, trauma associated with degeneration of the inner ear (R. PUJOL et al., Neuro report, 3, 299–302 (1992)) or the retina (J. L. MONSINGER et al., Exp. Neurol., 113, 10–17 (1991)), anxiety (KEHNE et al., Eur. J. Pharmacol., 193, 283 (1991)), depression (TRULLAS et al., Eur. J. Pharmacol., 185, 1 (1990)), schizophrenia (REYNOLDS, TIPS, 13, 116 (1992)), Tourette's syndrome and hepatic encephalopathies, as analgesics (DICKENSON et al., Neurosc. Letters, 121, 263 (1991)), anti-inflammatories (SLUTA et al., Neurosci. Letters, 149, 99–102 (1993)), antianorectics (SORRELS et al., Brain Res., 572, 265 (1992)), antimigraine drugs and antiemetics, and for treating poisoning by neurotoxins or other substances which are NMDA receptor agonists, as well as the neurological disorders associated with viral diseases such as AIDS (LIPTON et al., Neuron, 7, 111 (1991)), rabies, measles and tetanus (BAGETTA et al., Br. J. Pharmacol., 101, 776 (1990)). These compounds are also useful for prevention of the symptoms of drug and alcohol abstinence and of the inhibition of opiate addiction and dependence. They may also be used in the treatment of defects associated with mitochondrial abnormalities such as mitochondrial myopathy, Leber's syndrome, Wernicke's encephalopathy, Rett's syndrome, homocysteinaemia, hyperprolinaemia, hydroxybutiric/aminoaciduria, saturnine encephalopathy (chronic lead poisoning) and sulphite oxidase deficiency.

The affinity of the compounds of formula (I) for the AMPA receptor was determined by studying the antagonism of the specific binding of [$^3$H]AMPA to membranes of rat cerebral cortex (HONORE et al., Neuroscience letters, 54, 27 (1985)). [$^3$H]AMPA is incubated in the presence of 0.2 mg of proteins at 4° C. for 30 minutes in 10 mM $KH_2PO_4$, 100 mM KSCN buffer, pH 7.5. Non-specific binding is determined in the presence of 1 mM L-glutamate. Bound radioactivity is separated by filtration on Pharmacia filters (Printed Filtermate A). The inhibitory activity of these products is less than or equal to 100 $\mu$M.

The affinity of the compounds of formula (I) for the glycine site linked to the NMDA receptor was determined by studying the antagonism of the specific binding of [$^3$H] DCKA to membranes of rat cerebral cortex according to the method described by T. CANTON et al., J. Pharm. Pharmacol., 44, 812 (1992). [$^3$H]DCKA (20 nM) is incubated in the presence of 0.1 mg of proteins at 4° C. for 30 minutes in 50 mM HEPES buffer, pH 7.5. Non-specific binding is determined in the presence of 1 mM glycine. Bound radioactivity is separated by filtration on Whatman GF/B filters. The inhibitory activity of these products is less than or equal to 100 $\mu$M.

The compounds of formula (I) possess low toxicity. Their $LD_{50}$ is greater than 50 mg/kg via the IP route in mice.

Preferred compounds of formula (I) are those for which R represents a CH—$R_6$ radical in which $R_6$ represents a hydrogen atom or an —NR $_{14}R_{15}$ radical, or R represents a C=$R_7$ radical in which $R_7$ represents a CH—$R_{19}$ radical and $R_{19}$ represents an -alk-$COOR_{10}$ radical, or R represents a C(R4)R5 radical in which $R_4$ represents an alkyl radical and $R_5$ represents an -alk-$COOR_{10}$ radical, $R_1$ represents a hydrogen or halogen atom or an —NH—CO—$NR_{11}R_{12}$ radical and $R_2$ represents a hydrogen atom.

Preferably, the radical $R_1$ is at position 7 or 8.

Among these compounds, the preferred ones are the following:

1,4-dihydro-5H-indeno [1,2-b]pyrazine-2,3-dione,
8-chloro-1,4-dihydro-5H-indeno [1,2-b]pyrazine-2,3-dione.
(5-methyl-2,3-dioxo-1,4-dihydro-5H-indeno [1,2-b] pyrazin-5-yl)acetic acid,
5-amino-8-chloro-1,4-dihydro-5H-indeno [1,2-b]pyrazine-2,3-dione,
7-(3-phenylureido)-1,4-dihydro-5H-indeno [1,2-b]pyrazine-2,3-dione,
(E)-5-carboxymethylene-8-chloro-1,4-dihydroindeno[1,2-b]pyrazine-2,3-dione,
(8-chloro-5-methyl-2,3-dioxo-1,4-dihydro-5H-indeno[1,2-b]pyrazin-5-yl)acetic acid,
(+)-(5-methyl-2,3-dioxo-1,4-dihydro-1H-indeno [1,2-b] pyrazin-5-yl)acetic acid,
(−)-(5-methyl-2,3-dioxo-1,4-dihydro-1H-indeno [1,2-b] pyrazin-5-yl)acetic acid,
(+)-(8-chloro-5-methyl-2,3-dioxo-1,4-dihydro-5H-indeno [1,2-b]pyrazin-5-yl)acetic acid,
(−)-(8-chloro-5-methyl-2,3-dioxo-1,4-dihydro-5H-indeno [1,2-b]pyrazin-5-yl) acetic acid, and their salts.

The examples which follow illustrate the invention.

EXAMPLE 1

1.25 g of 2-ethoxalylamino-1-indanone are added rapidly to a solution of 12.5 g of ammonium acetate in 50 ml of acetic acid brought to reflux under nitrogen. After 18 hours of reflux, the reaction medium is cooled to a temperature in the region of 20° C. The precipitate formed is filtered off, washed copiously with water and dried under a partial vacuum (1 mm Hg; 0.13 kPa) at 50° C. 0.77 g of 1,4-dihydro-5H-indeno[1,2-b]pyrazine-2,3-dione are thereby obtained in the form of a green powder, the melting point of which is above 260° C. (analysis $C_{11}H_8N_2O_2$; 1.18 $H_2O$; % calculated C: 66.00; H: 4.03; N: 13.99; % found C: 65.7; H: 3.9; N: 13.9).

2-Ethoxalylamino-1-indanone may be prepared according to the following protocol: 6 g of 2-amino-1-indanone hydrochloride and 26.7 ml of ethoxalyl chloride are dissolved in 300 ml of tetrahydrofuran and stirred under nitrogen. 26.7 ml of triethylamine are added dropwise to the reaction mixture, and the reaction is continued for 90 minutes at a temperature in the region of 20° C. The mixture is then filtered through Celite and the filtrate concentrated to dryness under reduced pressure (15 mm Hg; 2 kPa). The residue is purified by flash chromatography on a silica column using a mixture of ethyl acetate and cyclohexane (20:80 by volume) as eluant. 1.5 g of expected product are thereby obtained in the form of an orange-coloured solid melting at 135° C.

2-Amino-1-indanone hydrochloride may be obtained in the following manner: a solution of sodium ethylate, prepared from 15.2 g of sodium and 770 ml of absolute ethanol, is added dropwise at 0° C. and under nitrogen to 200 g of 1-indanone oxime p-toluenesulphonate dissolved in 3.7 litres of anhydrous toluene. The reaction is continued for 40 hours at 0° C. The suspension is then filtered through Celite and the filtrate washed with water (400 ml). The toluene solution is treated with IN hydrochloric acid (4×400 ml) and the aqueous phase concentrated to dryness under reduced pressure (15 mm Hg; 2 kPa) at 40° C. The residue obtained is taken up in acetone, filtered off and dried to yield 29.8 g of expected product in the form of a brown solid which decomposes on heating.

1-Indanone oxime p-toluenesulphonate may be prepared in the following way: 532 g of p-toluenesulphonyl chloride dissolved in 600 ml of pyridine are added dropwise to 186.1 g of 1-indanone oxime dissolved in 900 ml of pyridine at 0° C. and under nitrogen. After 3 hours of reaction at 0° C., the reaction medium is poured into 3 litres of ice-cold water. The precipitate formed is filtered off, washed with water and dried. 354 g of expected product are thereby obtained in the form of a white solid melting at 150° C.

1-Indanone oxime may be obtained in the following manner: 366 g of hydroxylamine hydrochloride, 366 g of potassium carbonate and 340 ml of distilled water are added to 200 g of 1-indanone dissolved in 3.4 litres of methanol. The mixture is brought to reflux for 18 hours. After cooling, the suspension formed is filtered, and the residue is washed with water and then with methanol and dried under reduced pressure (1 mm Hg; 0.13 kPa) to yield 186.1 g of expected product in the form of a white solid melting at 154° C.

EXAMPLE 2

35 g of ammonium acetate are solubilized in 70 ml of acetic acid. 12.2 g of 6-chloro-2-ethoxalylamino-1-indanone are added to this solution and the mixture is brought to reflux for 6 hours. The reaction medium is then concentrated to dryness under reduced pressure (15 mm Hg; 2 kPa), and the oil obtained taken up with 100 ml of distilled water. The precipitate formed is filtered off, washed with water and dried under a partial vacuum (1 mm Hg; 0.13 kPa) at 40° C.

8.05 g of 8-chloro-1,4-dihydro-5H-indeno [1,2-b]pyrazine-2,3-dione are obtained in the form of a brown solid, the melting point of which is above 260° C. (NMR spectrum: [300 MHz; $(CD_3)_2SO$-$d_6$; δ in ppm]: 3.56 (s, 2H: —C$\underline{H}_2$-9); 7.15 (dd, J=8 and 2 Hz, 1H: —$\underline{H}$7); 7.43 (dd, J=8 Hz, 1H: —$\underline{H}$8); 7.62 (d, J=2 Hz, 1H: —$\underline{H}$5); from 11.75 to 12.75 (widely spread unres. comp.: —N$\underline{H}$CO—)).

6—Chloro-2-ethoxalylamino-1-indanone may be obtained in the following manner: in a three-necked flask cooled to 0C, 8.4 g of 2-amino-6-chloro-1-indanone hydrochloride are suspended in 100 ml of tetrahydrofuran, 5.53 ml of ethoxalyl chloride dissolved in 30 ml of the same solvent are then added and lastly 12.7 ml of triethylamine dissolved in 70 ml of tetrahydrofuran are added dropwise so that the temperature does not rise. The reaction is continued for 2 hours, during which the temperature rises slowly to 20° C. The precipitate formed is filtered off on Celite and the filtrate concentrated to dryness under reduced pressure. The residue obtained is taken up in 50 ml of ethyl ether, filtered off and dried under a partial vacuum (1 mm Hg; 0.13 kPa) at 40° C. 9.3 g of expected product are thereby obtained in the form of a brown solid melting at 153° C.

2-Amino-6-chloro-1-indanone hydrochloride is prepared in the same way as in Example 1 for the preparation of 2-amino-1-indanone, starting from 57.5 g of 6-chloro-1-indanone oxime p-toluenesulphonate, 3.94 g of sodium, 200 ml of absolute ethanol and 1 litre of anhydrous toluene. After 15 hours of reaction at 0° C., the precipitate formed is filtered off on Celite, the filtrate washed with water and then extracted with 1N hydrochloric acid (2×500 ml) and the aqueous phase concentrated to dryness under reduced pressure. 10.5 g of expected product are obtained in the form of a brown-green solid, the melting point of which is above 260° C.

6—Chloro-1-indanone oxime p-toluenesulphonate may be prepared according to the protocol described in Example 1 for the preparation of 1-indanone oxime p-toluenesulphonate, starting from 33 g of 6-chloro-1-indanone oxime, 69.3 g of p-toluenesulphonyl chloride and 330 ml of pyridine. 57.5 g of expected product are obtained in the form of a beige solid melting at 170° C.

6—Chloro-1-indanone oxime may be prepared according to the protocol described in Example 1 for the preparation of 1-indanone oxime, starting from 32.4 g of 6-chloro-1-indanone, 47.3 g of hydroxylamine hydrochloride, 47 g of potassium carbonate, 53 ml of distilled water and 530 ml of methanol. 33 g of expected product are obtained in the form of a yellow solid melting at 167° C.

6—Chloro-1-indanone may be prepared according to the process described by R. Sieka and W. Kellermann, Chem. Ber., 75, 1730 (1942).

EXAMPLE 3

A mixture of 0.7 g of ethyl (5-methyl-2,3-dioxo-1,4-dihydro-5H-indeno [1,2-b]pyrazin-5-yl)acetate, 40 ml of dioxane and 9 ml of 8N hydrochloric acid is heated to 40° C. for 90 hours. The reaction mixture is then evaporated in a rotary evaporator, and the evaporation residue is triturated in 20 ml of water, filtered off and rinsed with distilled water (2×10 ml) and then with isopropyl ether (10 ml). After drying at 60° C. under vacuum (1 mm Hg; 0.13 kPa), 0.4 g of (5-methyl-2,3-dioxo-1,4-dihydro-5H-indeno [1,2-b] pyrazin-5-yl)acetic acid is obtained in the form of a pale yellow solid melting above 260° C. (Analysis % calculated C: 61.76; H: 4.44; N: 10.29; O: 23.51; % found C: 61.8; H: 4.6; N: 10.4).

Ethyl (5-methyl-2,3-dioxo-1,4-dihydro-5H-indeno [1,2-b]pyrazin-5-yl)acetate may be prepared in the following way: a mixture of 2.1 g of ethyl N-(1-ethoxycarbonylmethyl-1-methyl-3-oxo-2-indanyl)oxamate, 20 ml of acetic acid and 4.6 g of ammonium acetate is heated to reflux for 4 hours. The reaction mixture is then concentrated in a rotary evaporator, 50 ml of water are added and the mixture is subjected to two extractions with ethyl acetate (2×50 ml). The organic extract is dried over magnesium sulphate, filtered and evaporated in a rotary evaporator. The yellow oil obtained (2 g) is purified by crystallization in 15 ml of acetonitrile. After filtration and washing of the crystals with 2×10 ml of acetonitrile and 2×10 ml of isopropyl ether, 0.7 g of ethyl (5-methyl-2,3-dioxo-1,4-dihydro-5H-indeno [1,2-b]pyrazin-5-yl) acetate is obtained in the form of a pale yellow solid ($^1$H NMR spectrum [300 MHz, $(CD_3)_2SO$-$d_6$, δ in ppm]: 0.77 (t, J=7 Hz, 3H: ethyl $CH_3$); 1.40 (s, 3H: $CH_3$); 3.00 (limiting AB, 2H: $CH_2$); 3.20 (q, J=7 Hz, 2H: ethyl $COOCH_2$); 7.12 and 7.25 (2 t, J=8 Hz, 2H: H 6 and H 7); 7.43 and 7.50 (2 d, J=8 Hz, 2H: H 5 and H 8)).

Ethyl N-(1-ethoxycarbonylmethyl-1-methyl-3-oxo-2-indanyl)oxamate may be prepared in the following manner: a mixture of 5.5 g of ethyl (2-amino-1-methyl-3-oxo-1-indanyl)acetate hydrochloride and 100 ml of dichloromethane is cooled to a temperature in the region of 20° C., 2.6 ml of ethoxalyl chloride are added, and a solution of 6.1 ml of triethylamine in 20 ml of dichloromethane is then added slowly while the temperature of the reaction medium is maintained close to 0° C. When the addition is complete, the temperature of the reaction mixture is allowed to rise to about 20° C. The mixture is then filtered and the filtrate is washed with distilled water (2×80 ml). The organic solution is dried over magnesium sulphate, filtered and evaporated in a rotary evaporator to give 6.2 g of ethyl N-(1-ethoxycarbonylmethyl)-1-methyl-3-oxo-2-inddanyl) oxamate in the form of a brown oil ($^1$H NMR spectrum [200 MHz, $(CD_3)_2SO$-$d_6$, δ in ppm]. A 50:50 mixture of isomers is observed: 0.88-1.03 and 1.34 (3 t, J=7 Hz, respectively 1.5H, 1.5H and 3H: ethyl $CH_3$); 1.21 and 1.65 (2 s, 1.5H each: $CH_3$); 2.75 and 3.03 (2 AB, respectively J=15 Hz and J=16 Hz, 2H in total: $CH_2$); 3.78, 3.92 and 4.32 (3 mts, 4H in total: ethyl $COOCH_2$); 4.81 and 5.10 (2 d, J=9 Hz, 1H in total: CH); from 7.40 to 7.85 (mt, 4H, aromatic H); 8.47 and 9.29 (2 d broad, J=9 Hz, 1H in total: NHCO)).

Ethyl (2-amino-1-methyl-3-oxo-1-indanyl)-acetate hydrochloride may be prepared in the following way: a solution of 7.32 g of ethyl (2-hydroxyimino-1-methyl-3-oxo-1-indanyl)acetate hydrochloride in 150 ml of acetic acid is saturated with gaseous hydrochloric acid, and the mixture is then hydrogenated for 20 hours at a pressure of 1.8 bar of hydrogen at a temperature in the region of 20° C. in the presence of 1.4 g of palladium on charcoal (palladium content 10%). The reaction mixture is filtered and concentrated in a rotary evaporator. The evaporation residue is treated with 50 ml of ethyl acetate, and 100 ml of ethyl ether are added slowly to the brown solution obtained. The white precipitate which appears is filtered off, washed with ethyl ether (2×50 ml) and dried. 5.5 g of ethyl (2-amino-1-methyl-3-oxo-1-indanyl)acetate hydrochloride are obtained in the form of an off-white solid melting at about 172° C. with decomposition ($^1$H NMR spectrum [300 MHz, $(CD_3)_2SO$-$d_6$, δ in ppm]. A 60:40 mixture of isomers is observed: 0.86-1.06 (2 t, J=7 Hz, 3H in total: ethyl $CH_3$); 1.36 and 1.75 (2 s, 3H in total: $CH_3$); 2.92, 3.20 and 3.46 (respectively limiting AB and 2 d (J=16 Hz), 2H in total: $CH_2$); 3.80 and 3.96 (2 mts, 2H in total: ethyl $COOCH_2$); 4.22 and 4.50 (2 s, 1H in total: CH); from 7.40 to 7.90 (mt, 4H: aromatic H); 8.94 (unres. comp., 3H in total: $NH_3^+$ $Cl^-$)).

Ethyl (2-hydroxyimino-1-methyl-3-oxo-1-indanyl) acetate hydrochloride may be prepared according to the process described in U.S. Pat. No. 3,703,529.

EXAMPLE 4

0.39 g of 5-acetamido-8-chloro-1,4-dihydro-5H-indeno [1,2-b]pyrazine-2,3-dione suspended in 5 ml of 6N hydrochloric acid is brought to reflux for 5 hours. After cooling to a temperature in the region of 20° C., the insoluble matter is filtered off, washed with water and then with methanol and taken up in 10 ml of a mixture of hot water and methanol (50:50 by volume). After a few minutes of stirring, the insoluble matter is filtered off and dried under a partial vacuum (1 mm Hg; 0.13 kPa) to yield 0.1 g of 5-amino-8-chloro-1,4-dihydro-5H-indeno [1,2-b]pyrazine-2,3-dione hydrochloride in the form of a grey solid, the melting point of which is above 260° C. ($^1$H NMR spectrum [250 MHz, $(CD_3)_2SO\text{-}d_6$, δ in ppm): 5.15 (s, 1H: CH 9); 7.39 (dd, J=8 and 2 Hz, 1H: H 7); 7.71 (d, J=2 Hz, 1H: H 5); 7.75 (d, J=8 Hz), 1H: H 8); from 8.70 to 9.20 (spread unres. comp., 3H: $NH_3^+Cl^-$); from 12.00 to 12.70 (spread unres. comp., 2H: NHCOCONH).

5-Acetamido-8-chloro-1,4-dihydro-5H-indeno [1,2-b] pyrazine-2,3-dione may be prepared according to the following procedure: 1 g of zinc powder is added in small portions to 1.74 g of 5-hydroxyimino-8-chloro-1,4-dihydroindeno [1,2-b]-pyrazine-2,3-dione suspended in 35 ml of acetic acid. The reaction medium is then brought to 90° C. for 1 hour. After cooling to a temperature in the region of 20° C., 0.7 ml of acetic anhydride is added and stirring is continued at the same temperature for 48 hours. 50 ml of distilled water are then added to the reaction medium, and the insoluble matter is filtered off, washed with acetone and with methanol to yield 0.9 g of expected product in the form of a brown solid, the melting point of which is above 260° C. ($^1$H NMR spectrum [300 MHz, $(CD_3)_2SO\text{-}d_6$, δ in ppm): 1.94 (s, 3H: $COCH_3$) 5.70 (d, J=8 Hz, 1H: CH 9); 7.20 (dd, J=8 and 2 Hz, 1H: H 7); 7.33 (d, J=8 Hz, 1H: H 8); 7.60 (d, J=2 Hz, 1H: H 5); 8.40 (d, J=8 Hz, 1H: NHCO); 12.15 and 12.35 (2 unres. comp., 1H each: NHCOCONH).

5-Hydroxyimino-8-chloro-1,4-dihydroindeno[1,2-b] pyrazine-2,3-dione may be prepared in the following way: 1.07 g of 60% sodium hydride are added in small portions to 2.75 g of 8-chloro-1,4-dihydro-5H-indeno [1,2-b] pyrazine-2,3-dione dissolved in 45 ml of dimethyl sulphoxide. As soon as the gaseous evolution has ceased, 1.39 ml of isoamyl nitrite dissolved in 35 ml of dimethyl sulphoxide are added to the reaction medium over approximately 15 minutes. The reaction is continued for 1.5 hours at a temperature in the region of 20° C. The reaction medium is then poured onto 500 ml of ice and thereafter diluted with 100 ml of methanol. The precipitate is filtered off and washed with methanol to yield 2.44 g of expected product in the form of a black solid, which is used without further purification in the subsequent syntheses. ($^1$H NMR spectrum [200 MHz, $(CD_3)_2SO\text{-}d_6$ with addition of a few drops of $CD_3COOD\text{-}d_4$, δ in ppm]. The mixture is observed of the two isomers, syn and anti, in the proportions 65:35: 7.23 (dd, J=8 and 2 Hz, 1H: H 7); 7.51 and 8.01 (2 d, J=8 Hz, 1H in total: H 8); 7.56 and 7.63 (2 d, J=2 Hz, 1H in total: H 5).

EXAMPLE 5

1.92 ml of phenyl isocyanate are added at a temperature in the region of 20° C. to a solution of 1.5 g of 7-amino-1, 4-dihydro-5H-indeno [1,2-b]pyrazine-2,3-dione hydrochloride and 2.48 ml of triethylamine in 20 ml of dimethylformamide. After overnight stirring at the same temperature, the precipitate formed is filtered off, washed with water and dried under a partial vacuum (1 mm Hg; 0.13 kPa) at 40° C. to yield 1.4 g of 7-(3-phenylureido)-1,4-dihydro-5H-indeno [1,2-b]pyrazine-2,3-dione in the form of a greenish solid, the melting point of which is above 260° C. (Analysis $C_{18}H_{14}N_4O_3$; 4.0 $H_2O$; % calculated C: 64.66; H: 4.22; N: 16.76; % found C: 64.4; H: 4.5; N: 16.8; $^1$H NMR spectrum [250 MHz, $(CD_3)_2SO\text{-}d_6$, δ in ppm]: 3.58 (s, 2H $CH_2$ 9); 7.00 (t, J=7.5 Hz, 1H: aromatic H of the phenyl at para with respect to the ureido); 7.30 (t, J=7.5 Hz, 2H: aromatic H of the phenyl at meta with respect to the ureido); 7.50 (d, J=7.5 Hz, 2H: aromatic H of the phenyl at ortho with respect to the ureido); from 7.20 to 7.60 (mt, 2H: H 5 and H 6); 7.72 (s broad, 1H: H 8); 8.80 (s broad, 2H: ArNHCONH); 12.00 and 12.28 (2 unres. comp. 1H each: NHCOCONH).

7-Amino-1,4-dihydro-5H-indeno [1,2-b]pyrazine-2,3-dione hydrochloride may be obtained in the following manner: 100 ml of concentrated hydrochloric acid are added dropwise to 6 g of 7-nitro-1,4-dihydro-5H-indeno [1,2-b] pyrazine-2,3-dione suspended in 135 ml of methanol, followed by 4.27 g of iron powder and 27 ml of dimethylformamide. The reaction mixture is stirred for 1 hour at room temperature and then treated again with 4.27 g of iron powder and 27 ml of dimethylformamide. The reaction is continued for 2 hours at 80° C. and, after cooling to a temperature in the region of 20° C., the insoluble matter is filtered off, washed with methanol and dried to yield 5.1 g of expected product in the form of an ochre powder, the melting point of which is above 260° C.($^1$H NMR spectrum [250 MHz, $(CD_3)_2SO\text{-}d_6$ plus a few drops of $CD_3COOD\text{-}d_4$, δ in ppm]: 3.60 (s, 2H: $CH_2$ 9); 7.34 (d broad, J=8 Hz, 1H: H 6); 7.47 (s broad, 1H: R 8); 7.66 (d, J=8 Hz, 1H: H 5).

7-Nitro-1,4-dihydro-5H-indeno[1,2-b]pyrazine-2,3-dione may be prepared according to the following procedure: 5.35 g of potassium nitrate are added to a solution, cooled to −5° C., of 10 g of 1,4-dihydro-5H-indeno [1,2-b]pyrazine-2,3-dione in 170 ml of sulphuric acid in such a way that the temperature does not exceed 0° C. The reaction is continued for 3 hours at a temperature in the region of 20° C. The reaction medium is then added to ice, and the precipitate formed filtered off, washed with water and dried to yield 6 g of expected nitrated product in the form of an orange-coloured powder, the melting point of which is above 260° C. ($^1$H NMR spectrum [300 MHz, $(CD_3)_2SO\text{-}d_6$, δ in ppm]: 3.73 (s, 2H $CH_2$ 9); 7.71 (d, J=8 Hz, 1H: H 5); 8.27 (dd, J=8 and 2.5 Hz, 1H: H 6); 8.33 (s broad, 1H: H 8); from 12.10 to 12.70 (unres. comp. 2H: NHCOCONH).

EXAMPLE 6

0.94 g of sodium hydride is added gradually to 1 g of B-chloro-1,4-dihydro-5H-indeno [1,2-b]pyrazine-2,3-dione and 0.59 g of glyoxylic acid hydrate dissolved in 15 ml of dimethyl sulphoxide while the reaction medium is maintained at a temperature in the region of 20° C. After 18 hours of reaction at the same temperature, 5 ml of acetic acid are added to the reaction medium and the mixture is brought to reflux for 4 hours. After cooling, the mixture is filtered, and the black insoluble matter washed with water and with methanol, then taken up in 15 ml of methanol and stirred overnight at room temperature. The insoluble matter is filtered off, washed with acetone and dried under a partial vacuum (1 mm Hg; 0.13 kPa) at 35° C. 0.7 g of (E)-5-carboxymethylene-8-chloro-1,4-dihydroindeno [1,2-b] pyrazine-2,3-dione is thereby obtained in the form of a dark brown solid, the melting point of which is above 260° C. ($^1$H NMR spectrum [200 MHz, $(CD_3)_2SO\text{-}d_6$, δ in ppm]: 6.69 (s broad, 1H: =CH); 7.15 (d broad, J=8.5 Hz, 1H: H 7); 7.54 (s broad, 1H: H 5); 7.67 (d, J=8.5 Hz), 1H: H 8); from 11.5 to 13.00 (spread unres. comp., 2H: OH); 15.90 (unres. comp. 1H: COOH).

EXAMPLE 7

A mixture of 2.27 g of ethyl (8-chloro-5-methyl-2,3-dioxo-1,4-dihydro-5H-indeno [1,2-b]pyrazin-5-yl)acetate, 120 ml of dioxane and 25 ml of 8N aqueous hydrochloric acid solution is heated to a temperature in the region of 80° C. for 4 hours. The reaction mixture is then evaporated under reduced pressure, and the evaporation residue is triturated in 35 ml of an ethanol/water (85:15 by volume) mixture, filtered and washed with distilled water (2 times 10 ml). The product obtained is taken up in 68 ml of 0.1N aqueous sodium hydroxide solution. The insoluble matter is separated by filtration, and the filtrate is neutralized by adding 6.8 ml of 1N aqueous hydrochloric acid solution. The solid obtained is separated by filtration, washed with distilled water (2 times 5 ml) and dried in the air. 0.41 g of (8-chloro-5-methyl-2,3-dioxo-1,4-dihydro-5H-indeno[1,2-b]pyrazin-5-yl) acetic acid is thereby obtained in the form of an ochre-coloured solid melting above 300° C. ($^1$H NMR spectrum [200 MHz, $(CD_3)_2SO-d_6$, δ in ppm]: 1.39 (3H, s, $CH_3$); 2.93 (2H, m, —$CH_2$—CO); 7.19 (1H, dd, J=8 and 2 Hz, arom H); 7.48 (1H, d, J=8 Hz, arom H); 7.56 (1H, d, 2=2 Hz, arom H); 12.18 (1H, s, —NH—); 12.24, s, —NH); Analysis, % calculated C: 54.83; H: 3.61; Cl: 11.56; N: 9.13; 0: 20.87; % found C: 55.2; H: 3.4; Cl: 11.2; N: 9.0; O: 18.6).

Ethyl (8-chloro-5-methyl-2,3-dioxo-1,4-dihydro-5H-indeno [1,2-b]pyrazin-5-yl)acetate may be prepared in the same way as is described in Example 3 for the preparation of ethyl (5-methyl-2,3-dioxo-1,4-dihydro-5H-indeno[1,2-b] pyrazin-5-yl)acetate, but starting from 21.5 g of ethyl N-(5-chloro-1-ethoxycarbonylmethyl-1-methyl-3-oxo-2-indanyl) oxamate and 43.6 g of ammonium acetate in 400 ml of acetic acid. The brown oil obtained (32 g) is triturated in 50 ml of diethyl ether. After filtering off the solid obtained and washing with 2 times 10 ml of diethyl ether, 10 g of ethyl (8-chloro-5-methyl-2,3-dioxo-1,4-dihydro-5H-indeno [1,2-b]pyrazin-5-yl)acetate are thereby obtained in the form of a yellow solid, which is used in the subsequent syntheses without further purification.

Ethyl N-(5-chloro-1-ethoxycarbonylmethyl-1-methyl-3-oxo-2-indanyl)oxamate may be prepared in the same way as is described in Example 3 for the preparation of ethyl N-(1-ethoxycarbonylmethyl-1-methyl-3-oxo-2-indanyl) oxamate, but starting from 18 g of ethyl (2-amino-5-chloro-1-methyl-3-oxo-1-indanyl)acetate hydrochloride, 7.6 ml of ethoxalyl chloride and 17.5 ml of triethylamine in 200 ml of dichloromethane. 20 g of ethyl N-(5-chloro-1-ethoxycarbonylmethyl-1-methyl-3-oxo-2-indanyl)oxamate are thereby obtained in the form of a brown oil, which is used in the subsequent syntheses without further purification.

Ethyl (2-amino-5-chloro-1-methyl-3-oxo-1-indanyl) acetate hydrochloride may be prepared in the same way as is described in Example 3 for the preparation of ethyl (2-amino-1-methyl-3-oxo-1-indanyl)acetate hydrochloride, but starting from 20 g of ethyl (5-chloro-2-hydroxyimino-1-methyl-3-oxo-1-indanyl)acetate hydrochloride in 450 ml of acetic acid saturated with gaseous hydrochloric acid and in the presence of 4 g of palladium on charcoal (palladium content 10%). After churning in 200 ml of diethyl ether, 18.4 g of ethyl (2-amino-5-chloro-1-methyl-3-oxo-1-indanyl) acetate hydrochloride are thereby obtained in the form of a pale green-white solid melting at 134° C.

Ethyl (5-chloro-2-hydroxyimino-1-methyl-3-oxo-1-indanyl)acetate hydrochloride may be prepared in the following way: 26.7 ml of tert-butyl nitrite are added to a solution of 40 g of ethyl (5-chloro-1-methyl-3-oxo-1-indanyl)acetate in 150 ml of ethyl ether and 55 ml of a 5.5N ethereal hydrogen chloride solution cooled to a temperature in the region of 10° C. The reaction mixture is stirred for 2 hours at a temperature in the region of 25° C. and then concentrated to dryness under reduced pressure. The oily residue obtained is taken up in 30 ml of ethyl acetate and evaporated to dryness under reduced pressure. The latter operation is carried out 5 times in order to remove the excess tert-butyl nitrite by azeotropic distillation. 43.7 g of ethyl (5-chloro-2-hydroxyimino-1-methyl-3-oxo-1-indanyl) acetate hydrochloride are thereby obtained in the form of a pale yellow solid melting at 144° C.

Ethyl (5-chloro-1-methyl-3-oxo-1-indanyl)acetate may be prepared in the following way: 15 ml of oxalyl dichloride are added slowly to a mixture of 40 g of (5-chloro-1-methyl-3-oxo-1-indanyl)acetic acid and 0.5 ml of N,N-dimethylformamide in 400 ml of dichloromethane. After 3 hours at a temperature in the region of 25° C., 60 ml of ethanol are added slowly. The reaction mixture is left stirring for 12 hours and is then washed with 2 times 50 ml of saturated aqueous sodium hydrogen carbonate solution, 50 ml of distilled water and 100 ml of saturated aqueous sodium chloride solution, dried over magnesium sulphate and concentrated to dryness under reduced pressure. 41 g of ethyl (5-chloro-1-methyl-3-oxo-1-indanyl)acetate are thereby obtained in the form of a brown oil, which is used in subsequent syntheses without further purification.

(5-Chloro-1-methyl-3-oxo-1-indanyl)acetic acid may be prepared in the following way: a mixture of 74 g of 3-(4-chlorophenyl)-3-methylglutaric acid in 300 ml of concentrated sulphuric acid is heated to reflux for 24 hours. After returning to a temperature in the region of 25° C., the reaction medium is poured slowly into 1 litre of ice-cold water and is then extracted with 3 times 500 ml of ethyl acetate. The combined organic phases are washed with 3 times 500 ml of water and 500 ml of saturated aqueous sodium chloride solution, dried over magnesium sulphate and concentrated to dryness under reduced pressure. The crude oil (60 g) is triturated in 50 ml of ethyl ether. The solid obtained is separated by filtration, washed with 20 ml of ethyl ether and dried in the air. 48 g of (5-chloro-1-methyl-3-oxo-1-indanyl)acetic acid are thereby obtained in the form of a cream-coloured solid melting at 119° C.

3-(4-Chlorophenyl)-3-methylglutaric acid may be prepared in the following way: a solution of 110 g of 2,4-dicyano-3-methyl-3-(4-chlorophenyl)glutarimide in a mixture consisting of 470 ml of water, 470 ml of concentrated sulphuric acid and 300 ml of acetic acid is heated to reflux for 42 hours. After returning to a temperature in the region of 25° C., the reaction medium is poured into 2 litres of ice-cold water. The precipitate formed is separated by filtration, washed with 2 times 50 ml of distilled water and dried in the air. 76.3 g of 3-(4-chlorophenyl)-3-methylpentanedioic acid are thereby obtained in the form of a cream-coloured solid melting at 128° C.

2,4-Dicyano-3-methyl-3-(4-chlorophenyl)glutarimide may be prepared in the following way: 37 g of cyanoacetamide are added slowly at a temperature in the region of 5° C. to an ethanolic solution of sodium ethylate obtained by adding 10.2 g of sodium to 400 ml of ethanol. After 15 minutes, a solution of 110 g of ethyl 2-cyano-3-(4-chlorophenyl)-2-butenoate is added to the suspension obtained. The reaction mixture is stirred for 4 hours at a temperature in the region of 25° C. and is then poured into 500 ml of distilled water. The reaction medium is cooled to a temperature in the region of 5° C. and then acidified by adding 85 ml of concentrated aqueous hydrochloric acid solution. The precipitate is separated by filtration, washed with 2 times 50 ml of water and dried in the air. 112 g of 2,4-dicyano- 3-methyl-3-(4-chlorophenyl)glutarimide are thereby obtained in the form of a yellow solid melting at 258° C.

Ethyl 2-cyano-3-(4-chlorophenyl)-2-butenoate may be prepared in the following way: a mixture of 130 ml of 4-chloroacetophenone, 107 ml of ethyl cyanoacetate, 15.4 g of ammonium acetate and 48 ml of acetic acid in 200 ml of toluene is heated to reflux for 12 hours, removing the water formed during the reaction by azeotropic distillation. After returning to a temperature in the region of 25° C., the reaction mixture is diluted with 100 ml of toluene, washed with 2 times 100 ml of distilled water and with 100 ml of saturated aqueous sodium chloride solution, dried over magnesium sulphate and concentrated to dryness under reduced pressure. The crude oil obtained is distilled under reduced pressure (pressure in the region of 30 mm of Hg) and the fraction distilling between 140 and 180° C. is collected. 110 g of ethyl 2-cyano-3-(4-chlorophenyl)-2-butenoate are thereby obtained in the form of a thick yellow oil, which is used in the subsequent syntheses without further purification.

EXAMPLE 8

The procedure is as in Example 3 but starting from 1.2 g of ethyl (+)-(5-methyl-2,3-dioxo-1,4-dihydro-1H-indeno [1,2-b]pyrazin-5-yl)acetate, 70 ml of dioxane and 15 ml of 8N hydrochloric acid. The acid obtained (0.64 g) is purified by solubilization in 40 ml of distilled water and 0.2 g of sodium hydrogen carbonate, washing of this solution with 15 ml of ethyl acetate and acidification of the aqueous phase with 2.5 ml of 1N hydrochloric acid. After the addition of 12 g of sodium chloride, the precipitate formed is filtered off, washed with 5 ml of distilled water and then 10 ml of isopropyl ethyl and dried at 60° C. under vacuum (1 mmHg; 0.13 kPa). The acid thus purified (0.27 g) is converted to the sodium salt by dissolution in 10 ml of 0.1N sodium hydroxide, filtration and lyophilization. 0.28 g of (+)-(5-methyl-2,3-dioxo-1,4-dihydro-1H-indeno[1,2-b]pyrazin-5-yl)acetic acid is obtained in the form of the sodium salt, melting above 260° C. (Analysis, % calculated C: 57.15; H: 3.77; N: 9.52; Na: 7.81; O: 21.75; % found C: 57.1; N: 9.0; $\alpha_D^{20}$=+24.1 (water; c=0.5%)).

Using the procedure described above, but starting from 1.2 g of ethyl (−)-(5-methyl-2,3-dioxo-1,4-dihydro-1H-indeno [1,2-b]pyrazin-5-yl)acetate, 70 ml of dioxane and 15 ml of 8N hydrochloric acid, 0.27 g of (−)-(5-methyl-2,3-dioxo-1,4-dihydro-1H-indeno [1,2-b]pyrazin-5-yl)acetic acid is obtained in the form of the sodium salt, melting above 260° C. (Analysis, % calculated C: 57.15; H: 3.77; N: 9.52; Na: 7.81; O: 21.75; % found C: 57.2; H: 3.8; N: 9.1; $\alpha_D^{20}$=−23.6 (water; c=0.5%)).

Ethyl (+)-(5-methyl-2,3-dioxo-1,4-dihydro-1H-indeno [1,2-b]pyrazin-5-yl)acetate and ethyl (−)-(5-methyl-2,3-dioxo-1,4-dihydro-1H-indeno [1,2-b]pyrazin-5-yl)acetate are prepared by chromatography of the racemic product on a CHIRACEL OD DAICEL chiral column (250 mm in length and 60 mm in diameter) using as eluent an ethanol/heptane (70:30 by volume) mixture at a flow rate of 80 ml/minute. Starting from 3×1.1 g of ethyl (+/−)-(5-methyl-2,3-dioxo-1,4-dihydro-1H-indeno [1,2-b]pyrazin-5-yl) acetate, 1.57 g of ethyl (+)-(5-methyl-2,3-dioxo-1,4-dihydro-1H-indeno [1,2-b]pyrazin-5-yl)acetate are obtained in the form of a yellow solid ($\alpha_D^{20}$=+51.2 (methanol; c=0.5%)) and 1.52 g of ethyl (−)-(5-methyl-2,3-dioxo-1,4-dihydro-1H-indeno [1,2-b]pyrazin-5-yl)acetate are obtained in the form of a yellow solid ($\alpha_D^{20}$=+24.1 (water; c=0.5%)).

EXAMPLE 9

Using the procedure described in Example 8, but starting from ethyl (+)-(8-chloro-5-methyl-2,3-dioxo-1,4-dihydro-5H-indeno [1,2-b]pyrazin-5-yl)acetate, (+)-(8-chloro-5-methyl-2,3-dioxo-1,4-dihydro-5H-indeno [1,2-b]pyrazin-5-yl)acetic acid is obtained, and starting from ethyl (−)-(8-chloro-5-methyl-2,3-dioxo-1,4-dihydro-5H-indeno [1,2-b] pyrazin-5-yl)acetate, (−)-(8-chloro-5-methyl-2,3-dioxo-1,4-dihydro-5H-indeno [1,2-b]pyrazin-5-yl)acetic acid is obtained.

Ethyl (+)-(8-chloro-5-methyl-2,3-dioxo-1,4-dihydro-5H-indeno [1,2-b]pyrazin-5-yl)acetate and ethyl (−)-(8-chloro-5-methyl-2,3-dioxo-1,4-dihydro-5H-indeno [1,2-b]pyrazin-5-yl)acetate are prepared as described in Example 8, starting from the mixture ethyl (+/−)-(8-chloro-5-methyl-2,3-dioxo-1,4-dihydro-5H-indeno [1,2-b]pyrazin-5-yl)acetate.

The medicinal products according to the invention consist of a compound of formula (I) or a salt of such a compound, in the pure state or in the form of a composition in which it is combined with any other pharmaceutically compatible product, which may be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colouring, a coating (dragees) or a varnish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can also comprise substances other than diluents, for example wetting, sweetening, thickening, flavouring or stabilizing products.

The sterile compositions for parenteral administration can preferably be solutions, aqueous or non-aqueous, suspensions or emulsions. As a solvent or vehicle, it is possible to employ water, propylene glycol, a polyethylene glycol, vegetable oils, especially olive oil, injectable organic esters, for example ethyl oleate, or other suitable organic solvents. These compositions can also contain adjuvants, especially wetting, tonicity, emulsifying, dispersing and stabilizing agents. The sterilization may be carried out in several ways, for example by aseptic filtration, by incorporating sterilizing agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain, besides the active product, excipients such as cocoa butter, semi-synthetic glycerides or polyethylene glycols.

In human therapy, the compounds according to the invention are especially useful for the treatment and/or prevention of conditions which require the administration of an AMPA receptor antagonist or an NMDA receptor antagonist. These compounds are, in particular, useful for treating or preventing all ischaemias and especially cerebral ischaemia, the effects due to anoxia, the progression of neurodegenerative diseases, Huntington's chorea, Alzheimer's disease, amyotrophic lateral sclerosis, olivopontocerebellar atrophy and Parkinson's disease for epileptogenic and/or convulsive manifestations, for the treatment of cerebral and spinal trauma, trauma associated with degeneration of the inner ear or the retina, anxiety, depression, schizophrenia, Tourette's syndrome and hepatic encephalopathy, as analgesics, anti-inflammatories, antianorectics, antimigraine drugs and antiemetics, and for treating poisoning by neurotoxins or other substances which are NMDA receptor agonists, as well as the neurological disorders associated with viral diseases such as AIDS, rabies, measles and tetanus. These compounds are also useful for prevention of the symptoms of drug and alcohol abstinence and of the inhibition of opiate addiction and dependence, as well as for the treatment of defects associated with mitochondrial abnormalities such as mitochondrial myopathy, Leber's syndrome, Wernicke's encephalopathy, Rett's syndrome, homocysteinaemia, hyperprolinaemia, hydroxybutiric/aminoaciduria, saturnine encephalopathy (chronic lead poisoning) and sulphite oxidase deficiency.

Doses depend on the effect sought, the duration of the treatment and the administration route used; they are generally between 10 mg and 100 mg daily via the oral route for an adult, with single doses ranging from 5 mg to 50 mg of active substance.

Generally speaking, the doctor will determine the appropriate dosage in accordance with the age and weight and all other factors specific to the subject to be treated.

The examples which follow illustrate some compositions according to the invention:

EXAMPLE A

Hard gelatin capsules containing a 50 mg dose of active product and having the following composition are prepared according to the usual technique:

Compound of formula (I) . . . 50 mg
Cellulose . . . 18 mg
Lactose . . . 55 mg
Colloidal silica . . . 1 mg
Sodium carboxymethylstarch . . . 10 mg
Talc . . . 10 mg
Magnesium stearate . . . 1 mg

EXAMPLE B

Tablets containing a 50 mg dose of active product and having the following composition are prepared according to the usual technique:

Compound of formula (I) . . . 50 mg
Lactose . . . 104 mg
Cellulose . . . 40 mg
Povidone . . . 10 mg
Sodium carboxymethylstarch . . . 22 mg
Talc . . . 10 mg
Magnesium stearate . . . 2 mg
Colloidal silica . . . 2 mg
Mixture of hydroxymethylcellulose, glycerol and titanium oxide (72:3.5:24.5) q.s. 1 finished film-coated tablet weighing 245 mg

EXAMPLE C

An injectable solution containing 10 mg of active product and having the following composition is prepared:

Compound of formula (i) . . . 10 mg
Benzoic acid . . . 80 mg
Benzyl alcohol . . . 0.06 ml
Sodium benzoate . . . 80 mg
Ethanol, 95% . . . 0.4 ml
Sodium hydroxide . . . 24 mg
Propylene glycol . . . 1.6 ml
Water . . . q.s. 4 ml

We claim:

1. A compound of formula (I):

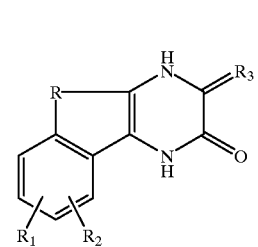

in which:
— R represents a $CR_4R_5$, $CHR_6$, or $C=R_7$ radical,
— $R_1$ and $R_2$, which may be identical or different, represent: (1) hydrogen, (2) halogen, (3) alkyl, (4) alkoxy, (5) amino, (6) —N=CH—N(alk)alk', (7) nitro, (8) cyano, (9) phenyl, (10) imidazolyl, (11) $SO_3H$, (12) hydroxyl, (13) polyfluoroalkoxy, (14) carboxyl, (15) alkoxycarbonyl, (16) —NH—CO—$NR_{11}R_{12}$, (17) —N(alk)—CO—$NR_{11}R_{12}$, (18) —N(alk—Ar)—CO—$NR_{11}R_{12}$, (19) —NH—CS—$NR_{11}R_{12}$, (20) —N(alk)—CS—$NR_{11}R_{12}$, (21) —NH—CO—$R_{11}$, (22) —NH—CS—$R_{24}$, (23) —NH—C(=$NR_{27}$)—$NR_{10}R_{12}$, (24) —N(alk)—C(=$NR_{27}$)—$NR_{10}R_{12}$, (25) —CO—$NR_{10}R_{12}$, (26) —NH—$SO_2$—$NR_{10}R_{12}$, (27) —N(alk)—$SO_2$—$NR_{10}R_{12}$, (28) —NH—$SO_2$—$CF_3$, (29) —NH—$SO_2$-alk, (30) —$NR_{10}R_{13}$, (31) —$S(O)_m$-alk-Ar, (32) —$SO_2$—$NR_{10}R_{12}$, (33) a 2-oxo-1-imidazolidinyl radical in which position 3 is substituted or unsubstitited with an alkyl radical, or (34) a 2-oxo-1-perhydropyrimidinyl radical in which position 3 is optionally substituted with an alkyl radical,
— $R_3$ represents an oxygen atom,
— $R_4$ represents an alkyl radical,
— $R_5$ represents an -alk-$COOR_{10}$ radical,
— $R_6$ represents a hydrogen atom or an $NR_{14}R_{15}$ radical,
— $R_7$ represents a $C(COOR_{10})R_{20}$ radical in which $R_{20}$ is a hydrogen atom,
— $R_{10}$ represents a hydrogen atom or an alkyl radical,
— $R_{11}$ represents: (1) hydrogen, (2) alkyl having from 1 to 9 carbon atoms in an unbranched or branched chain, (3) alkoxy, (4) -alk-$COOR_{10}$, (5) -alk-Het, (6) -alk-$NR_{12}R_{10}$, (7) phenylalkyl in which the phenyl ring is optionally substituted with one or more substituents selected from (a) halogen atoms, (b) alkyl, (c) alkoxy, (d) nitro, (e) amino, (f) hydroxyl, (g) -alk-$NH_2$, (h) carboxyl, (i) alkoxycarbonyl, (j) cyano and (k) -alk-$COOR_{10}$, or (8) a phenyl radical optionally substituted with one or more substituents selected from (a) halogen, (b) alkyl, (c) alkoxy, (d) nitro, (e) amino, (f)

hydroxyl, (g) -alk-$NH_2$, (h) carboxyl, (i) alkoxycarbonyl, (j) cyano, (k) -alk-$COOR_{10}$, and (l) a -Het radical, —$R_{12}$ represents a hydrogen atom or an alkyl radical, —$R_{13}$ represents an alkyl, Het or alkoxycarbonyl radical, —$R_{14}$ and $R_{15}$ each represent a hydrogen atom, —$R_{24}$ represents an alkyl radical, —$R_{27}$ represents a hydrogen atom or an alkyl radical, -alk represents an alkyl radical, -alk' represents an alkyl radical, —Ar represents a phenyl radical, —m is equal to 0, 1 or 2

-Het represents a saturated or unsaturated, mono- or polycyclic heterocycle containing 1 to 9 carbon atoms and one or more hetero atoms, said one or more hetero atoms being O, S, or N, optionally substituted with one or more alkyl, phenyl or phenylalkyl radicals, it being understood that the alkyl and alkoxy radicals contain 1 to 6 carbon atoms and are unbranched- or branched-chain radicals, the acyl radicals contain 2 to 4 carbon atoms, wherein acyl represents a —CO-alk radical in which the alkyl has 2 to 4 carbon atoms, it also being understood that the compound of formula (I) includes the E or Z isomer of a compound of formula (I) in which R represents a C=$R_7$ radical in which $R_7$ is a —C($COOR_{10}$)$R_{20}$ radical in which $R_{20}$ is a hydrogen atom; an enantiomer or diastereoisomer of a compound of formula (I) in which R represents a $CR_4R_5$ or $CHR_6$ radical; or a salt of a compound of formula (I).

2. The compound of formula (I) according to claim 1, wherein $R_1$ represents hydrogen, a halogen atom, or an NH—CO—$NR_{11}R_{12}$ radical and $R_2$ represents a hydrogen atom.

3. A compound selected from:
1,4-dihydro-5H-indeno[1,2-b]pyrazine-2,3-dione,
8-chloro-1,4-dihydro-5H-indeno[1,2-b]pyrazine-2,3-dione,
(5-methyl-2,3-dioxo-1,4-dihydro-5H-indeno[1,2-b]pyrazin-5-yl)acetic acid,
5-amino-8-chloro-1,4-dihydro-5H-indeno[1,2-b]pyrazine-2,3-dione,
7-(3-phenylureido)-1,4-dihydro-5H-indeno[1,2-b]pyrazine-2,3-dione,
(E)-5-carboxymethylene-8-chloro-1,4-dihydroindeno[1,2-b]pyrazine-2,3-dione,
(8-chloro-5-methyl-2,3-dioxo-1,4-dihydro-5H-indeno[1,2-b]pyrazin-5-yl)acetic acid,
(+)-(5-methyl-2,3-dioxo-1,4-dihydro-1H-indeno[1,2-b]pyrazin-5-yl)acetic acid,
(−)-(5-methyl-2,3-dioxo-1,4-dihydro-1H-indeno[1,2-b]pyrazin-5-yl)acetic acid,
(+)-(8-chloro-5-methyl-2,3-dioxo-1,4-dihydro-5H-indeno[1,2-b]pyrazin-5-yl)acetic acid,
(−)-(8-chloro-5-methyl-2,3-dioxo-1,4-dihydro-5H-indeno[1,2-b]pyrazin-5-yl)acetic acid, and the salts of said compounds.

4. A compound of formula (I) according to claim 1, wherein said $R_1$ substituent is at position 7 or 8.

5. A pharmaceutical composition for antagonizing an AMPA receptor which comprises a pharmaceutically effective amount of at least one compound of formula (I) according to claim 1 or a salt thereof with a pharmaceutically acceptable carrier.

6. A pharmaceutical composition for antagonizing an NMDA receptor which comprises a pharmaceutically effective amount of at least one compound of formula (I) according to claim 1 or a salt thereof with a pharmaceutically acceptable carrier.

* * * * *